US009266907B2

(12) United States Patent
Xue et al.

(10) Patent No.: US 9,266,907 B2
(45) Date of Patent: Feb. 23, 2016

(54) TUNABLE RARE-EARTH FCU-METAL-ORGANIC FRAMEWORKS

(71) Applicants: Dong-Xu Xue, Thuwal (SA); Amy J. Cairns, Thuwal (SA); Youssef Belmabkhout, Thuwal (SA); Mohamed Eddaoudi, Thuwal (SA)

(72) Inventors: Dong-Xu Xue, Thuwal (SA); Amy J. Cairns, Thuwal (SA); Youssef Belmabkhout, Thuwal (SA); Mohamed Eddaoudi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 60 days.

(21) Appl. No.: 14/019,511

(22) Filed: Sep. 5, 2013

(65) Prior Publication Data

US 2015/0065737 A1 Mar. 5, 2015

(51) Int. Cl.
C07F 5/00 (2006.01)
B01J 31/16 (2006.01)
C07C 51/41 (2006.01)

(52) U.S. Cl.
CPC ............... *C07F 5/00* (2013.01); *B01J 31/1691* (2013.01); *C07C 51/418* (2013.01)

(58) Field of Classification Search
CPC ..... C07F 5/003; B01J 31/1691; C07C 51/418
USPC .......................................................... 556/1
See application file for complete search history.

(56) References Cited

U.S. PATENT DOCUMENTS

| 7,652,132 | B2 | 1/2010 | Yaghi et al. |
| 7,799,120 | B2 | 9/2010 | Yaghi |
| 2004/0225134 | A1 | 11/2004 | Yaghi et al. |
| 2007/0068389 | A1 | 3/2007 | Yaghi |

FOREIGN PATENT DOCUMENTS

| WO | 2007035596 A2 | 3/2007 |
| WO | 2009035664 A1 | 3/2009 |
| WO | WO 2009/154374 | 12/2009 |

OTHER PUBLICATIONS

CrystEngComm, vol. 14, No. 13, pp. 4323-4334 (2012).*
Cavka et al., J. Am. Chem. Soc., vol. 130, No. 42, pp. 13850-13851 (2008).*
Wang et al., Chem. Commun, Vo. 47, pp. 7128-7130 (2011).*
Journal of The American Chemical Society, "Tunable Rare-Earth fcu-MOFs: A Platform for Systematic Enhancement of CO2 Adsorption Energetics and Uptake", Dong-Xu Xue et al., Apr. 22, 2013; 135, 7660-7667.
International Search Report PCT/US14/54224 dated Nov. 13, 2014.
Feng, et al., "Metal-Organic Frameworks Based on Previously Unknown Zr8/Hf8 Cubic Clusters", Inorganic Chemistry, vol. 52, Oct. 22, 2013, 12661-12667.
Zheng, et al., "Synthesis and characterization of two Novel Lanthanide Coordination Polymers with an Open Framework Based on an Unprecedneted [Ln7(u3-OH)8]13 Cluster", Inorganic Chemistry, 2004, pp. 1600-1602.
Partial International Search Report for International Application No. PCT/US2015/032441 mailed Oct. 28, 2015, 9 pages.

* cited by examiner

*Primary Examiner* — Porfirio Nazario Gonzalez
(74) *Attorney, Agent, or Firm* — Billion & Armitage; Benjamin C. Armitage

(57) ABSTRACT

Metal organic framework compostions can have a face centered cubic structure.

20 Claims, 36 Drawing Sheets

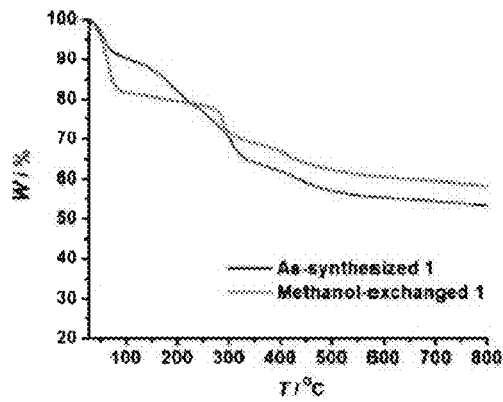
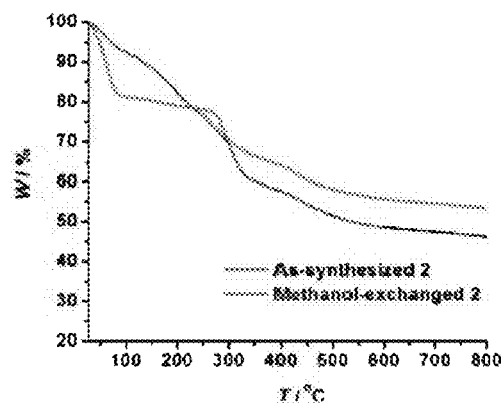
Figure 12A
Figure 12B
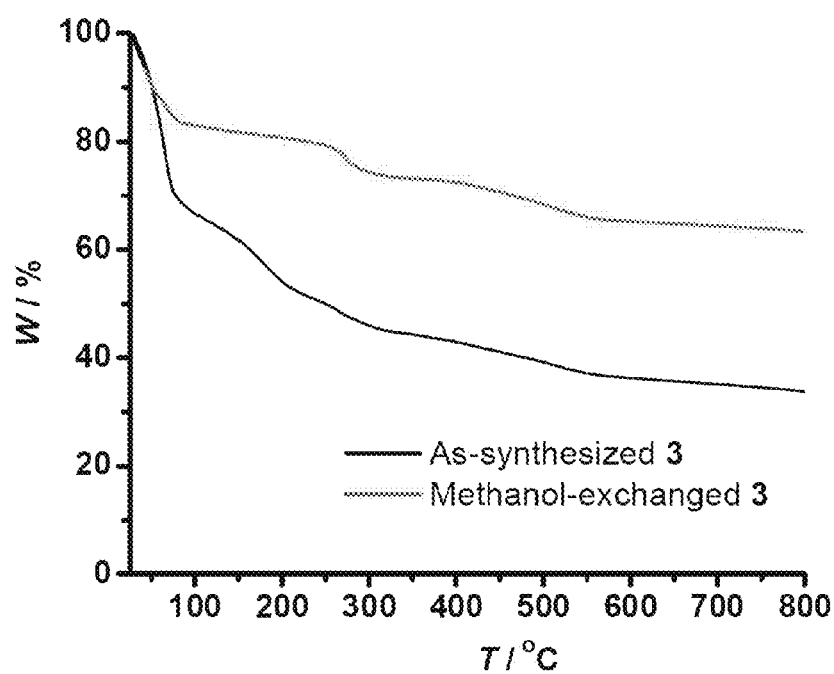
Figure 13

(a) (b)

(a) 
(b)

(a) 
(b)

TUNABLE RARE-EARTH FCU-METAL-ORGANIC FRAMEWORKS

TECHNICAL FIELD

This invention relates to metal-organic frameworks having tunable structures.

BACKGROUND

Metal-organic framework (MOF) materials can have tunable properties based on their structure, including porosity. Unique porous structures can allow the material to be used in applications including gas sequestration, storage and separation or scrubbing.

SUMMARY

A metal-organic framework composition can have a face centered cubic (fcu) structure. The composition can include a metal ion component and a bidentate ligand component having two anionic binding groups. The two anionic binding groups are oriented 180 degrees from each other. A plurality of the metal ion component and the bidentate ligand component associate to form a 12-connected face-centered cubic network.

A method of making a metal-organic framework composition can include contacting a metal ion component with a bidentate ligand component having two anionic binding groups, wherein the two anionic binding groups are oriented 180 degrees from each other, wherein the metal ion component and the bidentate ligand component associate to form a face-centered cubic network.

In some embodiments, the metal ion component includes a rare earth (RE) metal ion. For example, the rare earth metal ion is La, Ce, Pr, Nd, Sm, Eu, Gd, Dy, Ho, Er, Tm, Yb, Lu, Tb or Y, for example, terbium ($Tb^{3+}$) or yttrium ($Y^{3+}$).

In some embodiments, the two anionic binding groups can be the same. In some embodiments, the two anionic binding groups can be the different. In certain circumstances, each of the anionic binding groups, independently, is carboxylate or tetrazolate.

In some embodiments, the two anionic binding groups can be linked by an aromatic group.

In some embodiments, the aromatic group can include a hydrophobic group. For example, the hydrophobic group can be a fluoro group. The hydrophobic group can assist in the assembly of the fcu structure.

Other aspects, embodiments, and features will be apparent from the following description, the drawings, and the claims.

DESCRIPTION OF DRAWINGS

FIGS. 12A and 12B are graphs representing TGA plots of the as-synthesized and methanol-exchanged compounds 1-2.

FIG. 13 are graphs representing TGA plots of the as-synthesized and methanol-exchanged compound 3.

DETAILED DESCRIPTION

Figure 1:
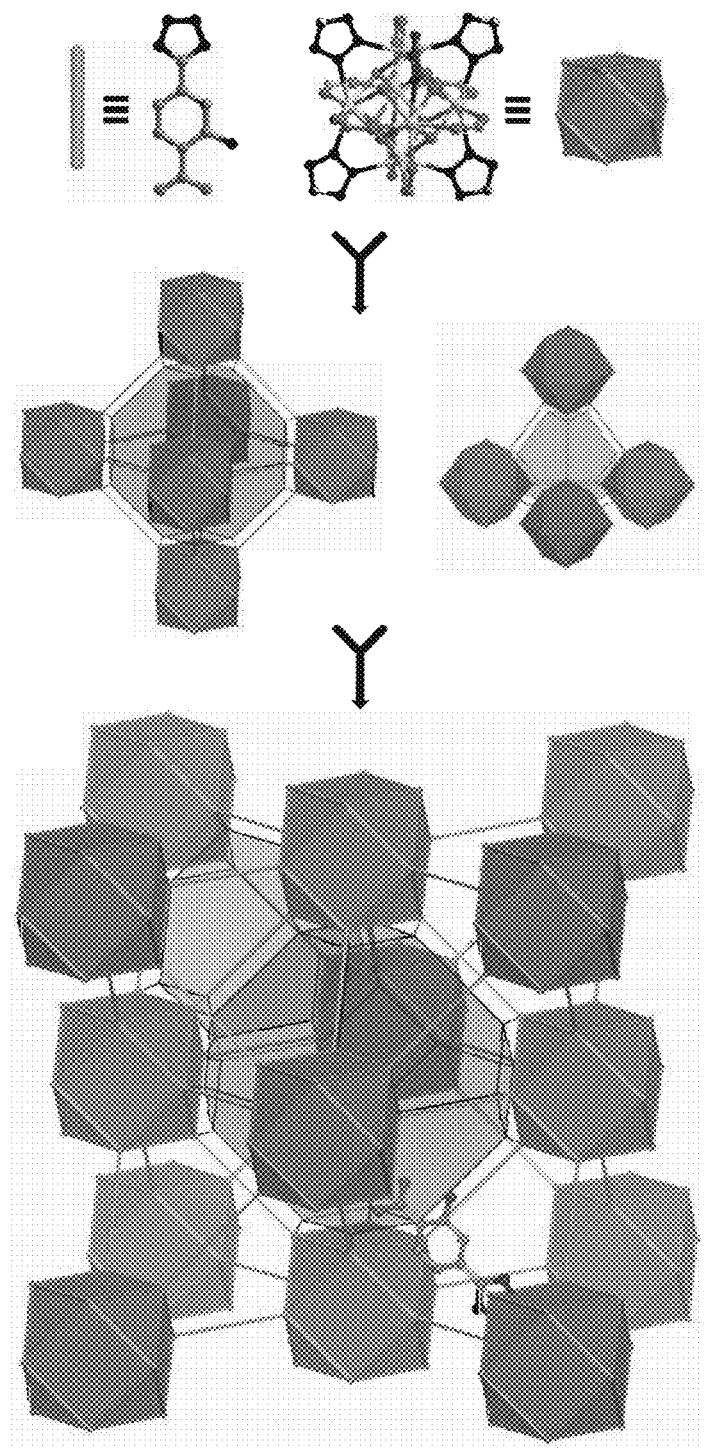
FIG. 1 is a drawing representing ball-and-stick and schematic representation of 1: From top to bottom, organic and inorganic MBBs, $FTZB^{2-}$ and the 12-connected Tb-based cluster, respectively, which can be viewed as a linear connection and cuboctahedron node to afford the augmented fcu net, consisting of octahedral and tetrahedral cages shown as blue and pink truncated polyhedron, respectively, Hydrogen atoms and coordinated water molecules are omitted for clarity. Tb=green, C=gray, N=blue, O=red, F=purple.

A metal-organic framework composition can have a face centered cubic (fcu) structure composed of metal ions and bidentate ligands. The metal ions and bidentate ligands for molecular building blocks that further form the fcu structure.

The molecular building block (MBB) approach has recently emerged as a powerful strategy for the design and construction of solid-state materials. See, e.g., Stein et al., Science 1993, 259, 1558-1564; Ferey, G., J. Solid State Chem. 2000, 152, 37-48; Eddaoudi et al., Science 2002, 295, 469-472; Kitagawa et al., Angew. Chem. Int. Ed. 2004, 43, 2334-2375; Moulton et al., Chem. Rev. 2001, 101, 1629-1658; Eddaoudi et al., Acc. Chem. Res. 2001, 34, 319-330; and U.S. Pat. No. 6,624,318 (each of which is incorporated by reference herein in its entirety). The molecular building block joins or otherwise associates with other molecular building blocks to form supramolecular structures. The molecular building block can be a 12-connected molecular building block. The 12-connected molecular building block can have 12 sites for ligand attachment to neighboring structures.

The metal ions can form a metal ion component of the composition. The metal ion can be an electron rich metal ion. For example, the metal ion can be a RE metal ion, for example, a lanthanide elements, such as an ion of La, Ce, Pr, Nd, Sm, Eu, Gd, Tb, Dy, Ho, Er, Tm, Yb, Lu, or Y. In certain circumstances, the metal ion is terbium or yttrium, e.g., $Tb^{+3}$ or $Y^{+3}$.

The bidentate ligand can form a bidentate ligand component of the composition. The bidentate ligand has two anionic binding groups. The two anionic binding groups, point away from each other. Specifically, the two anionic binding groups can be oriented 180 degrees from each other. The bidentate ligand can have the structure:

$$A1\text{-}L\text{-}A2 \qquad (I)$$

In formula (I), each A1 can be carboxyl, tetrazolyl, sulfonyl, or phosphoryl;

In formula (I), each A2 can be carboxyl, tetrazolyl, sulfonyl, or phosphoryl;

In preferred embodiments, A1 and A2 are each, independently, carboxyl or tetrazolyl.

In formula (I), L can be a divalent aryl, heteroaryl, carbocyclyl, or heterocyclyl, In preferred embodiments, L can be a 3- to 14 membered divalent monocyclic heterocyclyl, a 3- to 14 membered divalent aryl, or a 3- to 14 membered divalent heteroaryl. In preferred embodiments, L is substituted with 1, 2, 3, or 4 halo or halomethyl groups. For example, L can be an ortho substituted fluoro phenylene, naphthylene or diphenylene group.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, I,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo [2.1.1]hexyl, bicyclo[2.2.1]heptyl, bicyclo[2.2.1]heptenyl, 6,6-dimethylbicyclo[3.1.1]heptyl, 2,6,6-trimethylbicyclo [3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

The term "arylalkyl" refers to an alkyl group substituted with an aryl group. Representative examples of arylalkyl groups include, for example, benzyl, picolyl, and the like.

The term "phenylene" refers to a divalent phenyl.

The molecular building block can include bridging ligands, such as, for example, oxy, hydroxyl, sulfhydryl, or amino groups.

In the synthesis of the molecular building blocks, the molecular building block can have an overall ionic charge. Thus the molecular building block can be an anion or a cation and have one or more corresponding counterions, such as, for example, $H^+$, $Li^+$, $Na^+$, $K^+$, $Mg^+$, $Ca^{2+}$, $Sr^{2+}$, ammonium (including monoalkyl, dialkyl, trialkyl or tetraalkylalkyl ammonium), or one or $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, borate (including monoalkyl, dialkyl, trialkyl or tetraalkylalkyl borate) or $PF_6^-$, and organic counterions such as acetate or triflate.

The A1 and A2 groups are oriented at 180 degrees from each other. For example, when L is arylene, A1 and A2 are in a "para" or substantially "para" relative position. In a phenylene structure, A1 and A2 are at positions 1 and 4 on the ring; in a biphenylene structure, A1 and A2 are at positions 4 and 4'.

The method of making a MOF composition can include contacting a metal ion component with a bidentate ligand component having two anionic binding groups. A salt of the metal ion can be dissolved in a solvent and combined with the bidentate ligand. Optionally, other salts can be added to provide other counter ions in the final structure. The material is then crystallized from the combined solution. The presence of a hydrophobic group in the bidentate ligand, for example, a fluoro group ortho to the binding group, contributes to formation of the desired fcu structure. The bidentate ligand having a hydrophobic group can be present in a catalytic amount during formation of the final MOF.

A series of fcu-MOFs based on RE metals and linear fluorinated/non-fluorinated, homo-/hetero-functional ligands can be targeted and synthesized. This particular fcu-MOF platform was selected due to its unique structural characteristics combined with the ability/potential to dictate and regulate its chemical properties (e.g., tuning of the electron-rich rare-earth metal ions and high localized charge density, a property arising from the proximal positioning of polarizing tetrazolate moieties and fluoro-groups that decorate the exposed inner surfaces of the confined conical cavities). These features permitted a systematic gas sorption study to evaluate/elucidate the effects of distinctive parameters on $CO_2$-MOF sorption energetics. It shows the importance of the synergistic effect of exposed open metal sites and proximal highly localized charge density toward materials with enhanced $CO_2$ sorption energetics.

In recent years, there has been a strong scientific drive to minimize greenhouse gas emissions especially $CO_2$. See, for example, Chu, S. Science 2009, 325, 1599, which is incorporated by reference in its entirety. The release of $CO_2$ from flue gas and the automobile industry are the major contributors, and myriad efforts are underway to economically separate and capture the effluent $CO_2$. See, for example, The Center for Climate and Energy Solutions (C2ES), Reducing Greenhouse Gas Emissions from U.S. Transportation, 2011, Arlington; Sumida, K.; Rogow, D. L.; Mason, J. A.; McDonald, T. M.; Bloch, E. D.; Herm, Z. R.; Bae, T.-H.; Long, J. R. Chem. Rev. 2012, 112, 724-781, Vaidhyanathan, R.; Iremonger, S. S.; Shimizu, G. K. H.; Boyd, P. G.; Alavi, S.; Woo, T. K. Science 2010, 330, 650-653, each of which is incorporated by reference in its entirety. Highly porous sorbent materials have emerged as a plausible solution, and considerable efforts have been put forth to develop suitable materials. An optimal adsorbent for $CO_2$ separation should, in addition to high adsorption uptake and suitable kinetics, exhibit high affinity toward $CO_2$ to be translated into high interaction, which in turns plays a critical role in determining the adsorption selectivity and the energy required to release $CO_2$ during the regeneration step. Accordingly, the ideal isosteric heat of adsorption ($Q_{st}$) should permit reversible physical adsorption-desorption operation in a pressure or vacuum swing adsorption (PSA or VSA) process (i.e., $CO_2$— sorbent interactions are neither too strong nor too weak).

MOFs, a relatively new class of porous materials, appear well-poised to address the $CO_2$ challenge due to their mild synthesis conditions, relatively high thermal stability, large pore volumes, potentially exposed inner surface with high localized charge density, and readily programmable and modular construction (i.e., a given structure with the desired net topology; functionalizable isoreticular structures) from pre-designed molecular building blocks (MBBs). See, for example, Robson, R. J. Chem. Soc., Dalton Trans. 2000, 3735-3744; Férey, G. J. Solid State Chem., 2000, 152, 37-48; Eddaoudi, M.; Moler, D. B.; Li, H.; Chen, B.; Reineke, T. M.; O'Keeffe, M.; Yaghi, O. M. Acc. Chem. Res. 2001, 34, 319-330; Chun, H.; Dybtsev, D. N.; Kim, H.; Kim, K. Chem. Eur. J. 2005, 11, 3521-3529; Metal-Organic Frameworks: Design and Application; MacGillivray, L. R., Ed.; Wiley-VCH: Weinheim, Germany, 2010; Kitagawa, S.; Kitaura, R.; Noro, S.-I. Angew. Chem., Int. Ed. 2004, 43, 2334-2375; Férey, G. Chem. Soc. Rev. 2008, 37, 191-214, each of which is incorporated by reference in its entirety. As such, considerable effort has been dedicated to ascertaining the ideal $CO_2$-MOF interactions/energetics, but minimal systematic studies of finely-tuned MOFs have been reported. See, for example, Sumida, K.; Rogow, D. L.; Mason, J. A.; McDonald, T. M.; Bloch, E. D.; Herm, Z. R.; Bae, T.-H.; Long, J. R. Chem. Rev. 2012, 112, 724-781; Vaidhyanathan, R.; Iremonger, S. S.; Shimizu, G. K. H.; Boyd, P. G.; Alavi, S.; Woo, T. K. Science 2010, 330, 650-653, each of which is incorporated by reference in its entirety.

Development and isolation of novel MBBs can facilitate the rational construction of targeted functional MOFs. See, for example, Liu, Y.; Eubank, J. F.; Cairns, A. J.; Eckert, J.; Kravtsov, V. Ch.; Luebke, R.; Eddaoudi, M. Angew. Chem., Int. Ed. 2007, 46, 3278-3283, each of which is incorporated by reference in its entirety. The discovery of novel modular and rigid inorganic MBBs and establishing reaction conditions that permit to generate a specific inorganic MBB consistently in situ can be a vital criterion/prerequisite for the prospective design and rational construction of desired MOFs.

With the aim to construct porous MOFs with high localized charge density, a potential attribute to promote/enhance the $CO_2$ sorption energetics, porous MOFs with high localized charge density, a potential attribute to promote/enhance the $CO_2$ sorption energetics, can be prepared based on metal-ligand directed assembly of electron-rich RE metal ions and non-centrosymmetric hetero-functional ligands containing carboxylate and terazolate moieties. Hexanuclear RE-based ($Tb^{3+}/Y^{3+}$) MBBs, generated in situ, to construct a series of 12-connected MOFs can possess face centered cubic (fcu) topology. The MBBs are bridged in a linear fashion through an assortment of fluoro and/or tetrazolate functionalized organic ligands, as outlined in Scheme 1. Systematic gas sorption studies on these materials have elucidated the effects of distinctive parameters on $CO_2$-MOF sorption energetics.

Scheme 1. Representation of the organic linkers present in compounds 1-7.

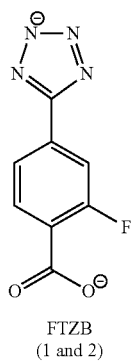

FTZB
(1 and 2)

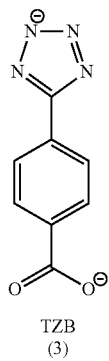

TZB
(3)

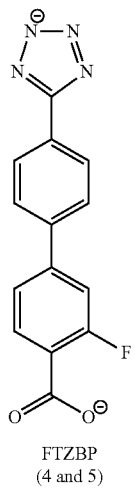

FTZBP
(4 and 5)

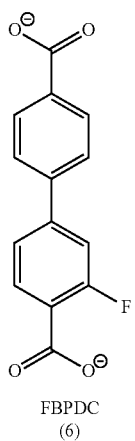

FBPDC
(6)

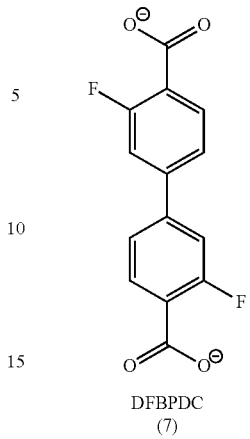

DFBPDC
(7)

EXAMPLES

A Series of Fcu-Mofs Based on Rare-earth Metals and Functional Ligands

Reactions are based on solvothermal reactions between RE metal salts (RE=Y, Tb) and asymmetric hetero-functional ditopic linkers (e.g., 2-fluoro-4-(1H-tetrazol-5-yl)benzoic acid ($H_2$FTZB) and 4-(1H-tetrazol-5-yl)benzoic acid ($H_2$TZB)) in various solvent mixtures. Reaction between $H_2$FTZB and Tb(NO$_3$)$_3$.5H$_2$O in an N,N'-dimethylformamide (DMF)/ethanol/chlorobenzene solution yielded transparent polyhedral crystals, formulated by single-crystal x-ray diffraction (SCXRD) studies as $$[((CH_3)_2NH_2)_2[Tb_6(\mu_3\text{-}OH)_8(FTZB)_6(H_2O)_6] \cdot (H_2O)_{22} \quad (1).$$

Compound 1 crystallizes in the cubic space group Fm-3m. In the crystal structure of 1, each $Tb^{3+}$ metal ion is surrounded by four $\mu_3$-OH groups, four oxygen and/or nitrogen atoms from statistically disordered carboxylate groups and/or tetrazolate rings from four independent FTZB$^{2-}$ ligands, leaving the ninth coordination site occupied by a water molecule (FIG. 1). The adjacent Tb ions are bridged via $\mu_3$-OH and deprotonated carboxylate and/or tetrazolate groups in a bis-monodentate fashion to give a [Tb$_6$($\mu_3$-OH)$_8$(O$_2$C—)$_6$(N$_4$C—)$_6$] MBB. Each hexanuclear MBB is bridged through FTZB$^{2-}$ to produce a 3-periodic MOF.

Structural/topological analysis of the resulting crystal structure reveals that 1 is a MOF with the face-centered cubic (fcu) topology (i.e., an fcu-MOF) constructed from the bridged hexanuclear clusters, [Tb$_6$($\mu_3$-OH)$_8$(O$_2$C—)$_6$(N$_4$C—)$_6$] MBBs, where the carbon atoms of the coordinated carboxylate and tetrazolate moieties, acting as points of extension, coincide with the cuboctahedron vertex figure of the quasiregular fcu net, the only 12-connected edge transitive net. Edge transitive nets possess only one kind of edge, and are ideal targets in crystal chemistry. See, for example, Friedrichs, O. D.; O'keeffe, M.; Yaghi, 0. M. *Acta Crystallogr.* 2003, A59, 22-27; Friedrichs, 0. D.; O'keeffe, M.; Yaghi, 0. M. *Acta Crystallogr.* 2003, A59, 515-525; Robinson, S. A. K.; Mempin, M.-V. L.; Cairns, A. J.; Holman, K. T. *J. Am. Chem. Soc.* 2011, 133, 1634-1637; Masciocchi, N.; Galli, S.; Colombo, V.; Maspero, A.; Palmisano, G.; Seyyedi, B.; Lamberti, C.; Bordiga, S. J. Am. Chem. Soc. 2010, 132, 7902-7904, each of which is incorporated by reference in its entirety. Replacement of the metal salt with Y(NO$_3$)$_3$.6H$_2$O in the same reaction mixture, resulted in the analogous fcu- MOF, [(CH$_3$)$_2$NH$_2$]$_2$[Y$_6$(μ$_3$-OH)$_8$(FTZB)$_6$(H$_2$O)$_6$].(H$_2$O)$_{52}$ (2). Similar reaction conditions for the non-fluorinated linker, H$_2$TZB, resulted in clear solutions. However, introduction of a fluorinated modulator, 2-fluorobenzoic acid, has permitted the successful construction of the desired TZB-based isostructural fcu-MOF, [(CH$_3$)$_2$NH$_2$]$_2$[Tb$_6$(μ$_3$-OH)$_8$(TZB)$_6$ (H$_2$O)$_6$].x(solvent) (3), as determined by SCXRD studies. Under the present reaction conditions, a fluoro-substituent located in the alpha (α) position relative to the carboxylate moiety can be necessary for the formation of the 12-connected RE-based MBB. The present hexanuclear clusters, based on mixed carboxylates and tetrazolates, are unprecedented, though a corresponding pure carboxylate molecular cluster based on cerium recently appeared in the open literature. See, for example, Mereacre, V.; Ako, A. M.; Akhtar, M. N.; Lindemann, A.; Anson, C. E.; Powell, A. K. *Helv. Chim. Acta* 2009, 92, 2507-2524; Das, R.; Sarma, R.; Baruah, J. B. *Inorg. Chem. Comm.* 2010, 13, 793-795, each of which is incorporated by reference in its entirety.

Occurrence of other analogous hexanuclear clusters in MOF chemistry is limited to a single Zr-based 12-coordinate MBB, where isostructural Zr$^{IV}$-based fcu-MOFs (e.g., UiO-66) based on [Zr$_6$(O)$_4$(OH)$_4$(O$_2$C—)$_{12}$] MBBs are linked together via linear homo-functional dicarboxylate ligands. See, for example, Cavka, J. H.; Jakobsen, S.; Olsbye, U.; Guillou, N.; Lamberti, C.; Bordiga, S.; Lillerud, K. P. *J. Am. Chem. Soc.* 2008, 130, 13850-13851; Schaate, A.; Roy, P.; Godt, A.; Lippke, J.; Waltz, F.; Wiebcke, M. and Behrens, P. *Chem. Eur. J.* 2011, 17, 6643-6651, each of which is incorporated by reference in its entirety.

fcu-MOFs based on RE metals can be constructed, and the [RE$_6$(μ$_3$-OH)$_8$(O$_2$C—)$_6$(N$_4$C—)$_6$] MBB, RE=Tb and Y can be consistently generated in situ. Such attributes combined with the fact that the fcu net is the only edge transitive net for the assembly of 12-connected cuboctahedron building units, permit the practice of reticular chemistry par excellence, rational MOF design, and thus access to a new MOF platform based on the fcu topology, where the metal ions and ligand functional groups and size to perform a systematic study on the effect of the structural changes on CO$_2$-MOF energetics can be methodically modified.

The fcu-MOF structure encloses two polyhedral cages, i.e., octahedral and tetrahedral, with effective accessible diameters estimated to be, in the case of compound 1, 14.5 and 9.1 Å (considering van der Waals radii), respectively. Access to the cages is permitted through shared triangular windows, ca. 5-6 Å, which are of suitable size for the adsorption of small gas molecules, e.g., Ar, H$_2$, CO$_2$, etc. The corresponding solvent accessible free volumes for 1 and 2 were estimated to be 63.0% and 63.8%, respectively, by summing voxels more than 1.2 Å away from the framework using PLATON software. See, for example, Spek, A. L. *Acta Crystallogr.* 1990, 46, c34, which is incorporated by reference in its entirety.

Figure 2:
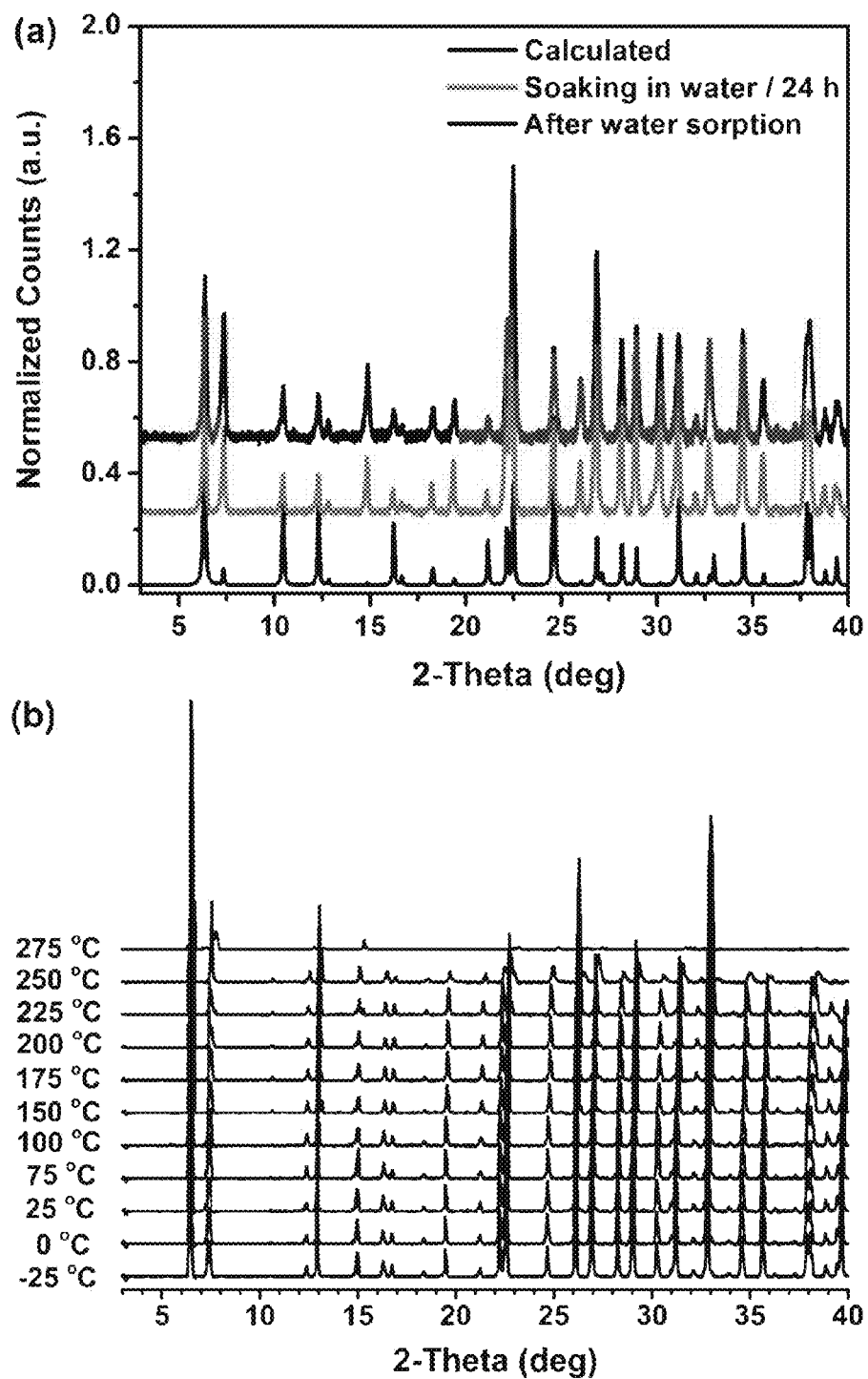
FIG. 2 are graphs representing PXRD patterns for compound 1: (a) after exposure to water and (b) variable temperature under a vacuum.
Figure 6A:
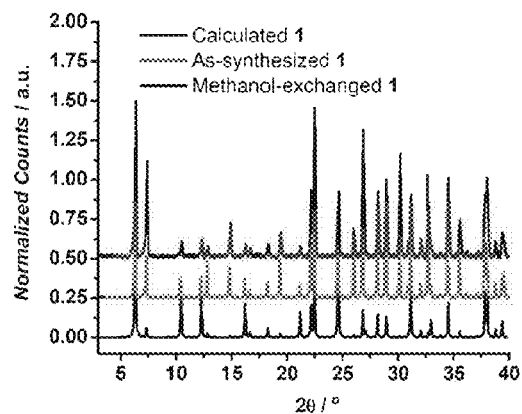
FIGS. 6A and 6B are graphs representing PXRD patterns of the as-synthesized, calculated and solvent-exchanged compounds 1-2, indicating the phase purity of as-synthesized and methanol-exchanged products.
Figure 6B:
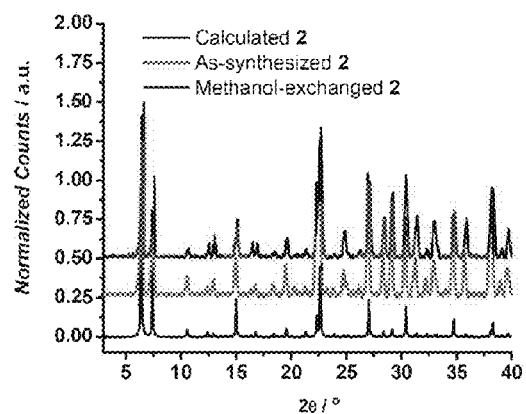
Figure 7:
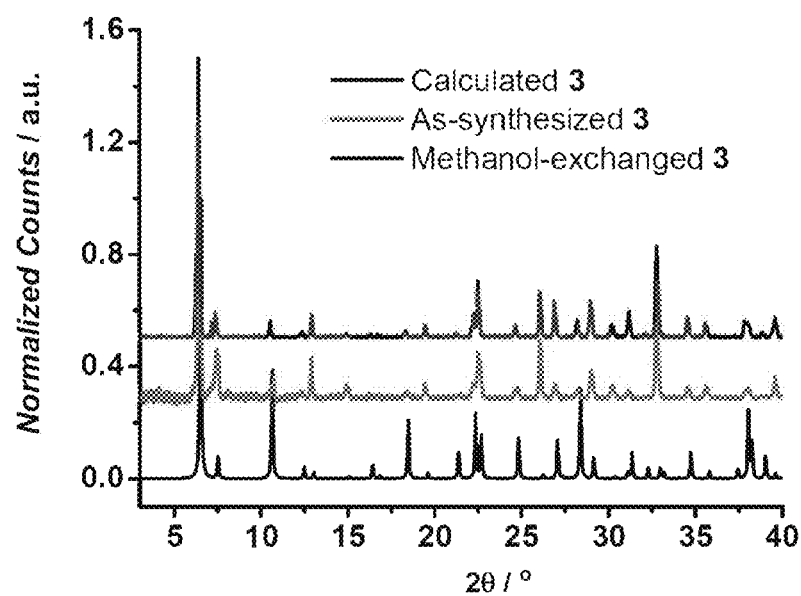
FIG. 7 is a graph representing PXRD patterns of the as-synthesized, calculated and solvent-exchanged compound 3, indicating the phase purity of as-synthesized and methanol-exchanged products.
Figure 8A:
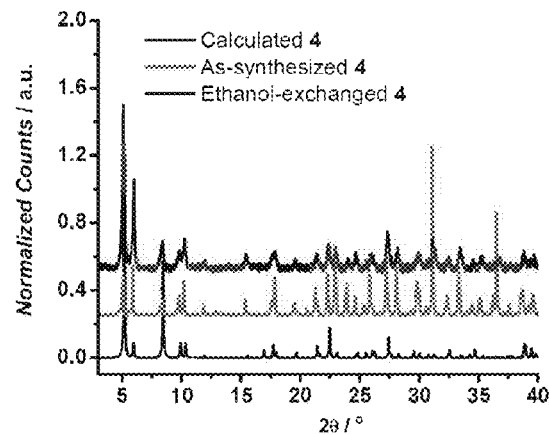
FIGS. 8A and 8B are graphs representing PXRD patterns of the as-synthesized, calculated and solvent-exchanged compounds 4-5, indicating the phase purity of as-synthesized and solvent-exchanged products.
Figure 8B:
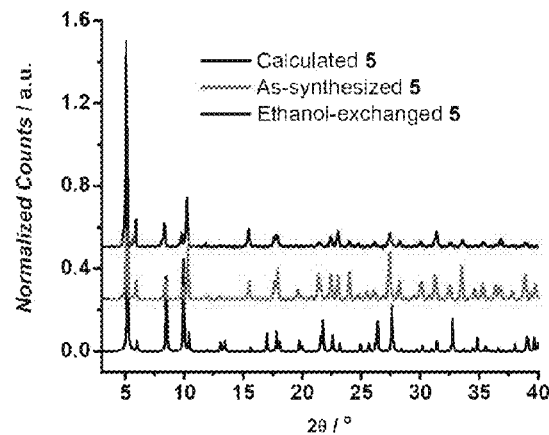
Figure 9A:
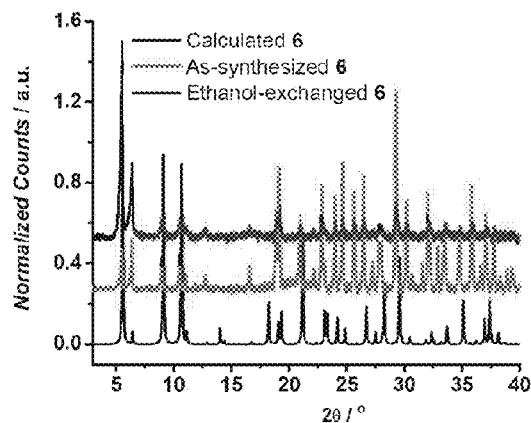
FIGS. 9A and 9B are graphs representing PXRD patterns of the as-synthesized, calculated and solvent-exchanged compounds 6-7, indicating the phase purity of as-synthesized and solvent-exchanged products.
Figure 9B:
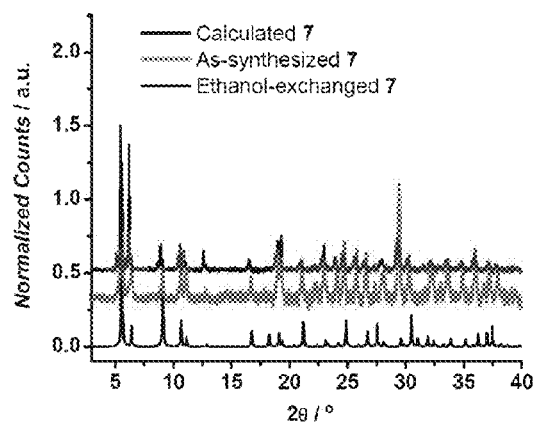
Figure 11:
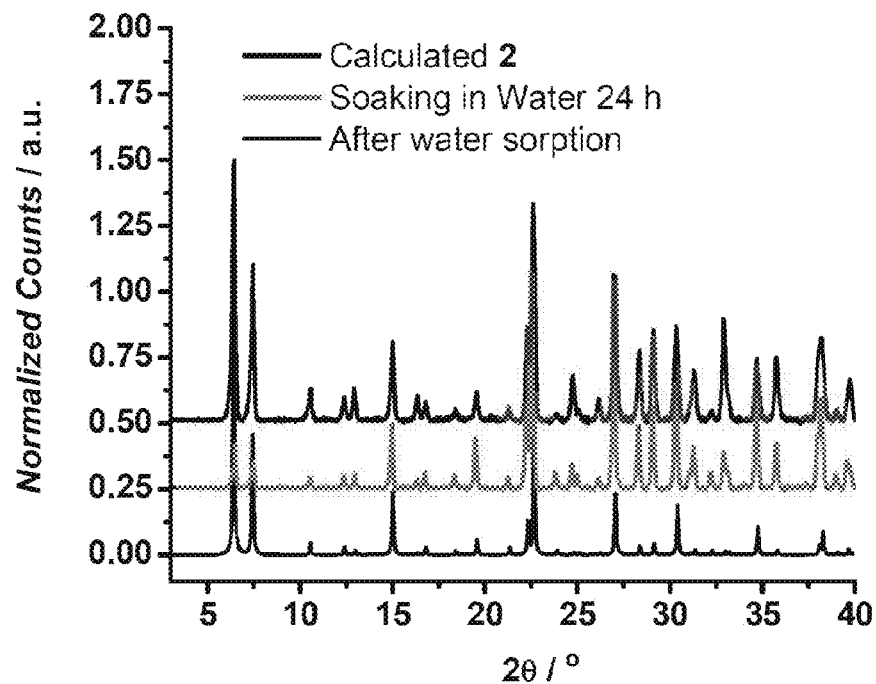
FIG. 11 is a graph representing PXRD patterns for compound 2 after exposure to water, indicating a highly chemical stability in aqueous media.
Figure 14A:
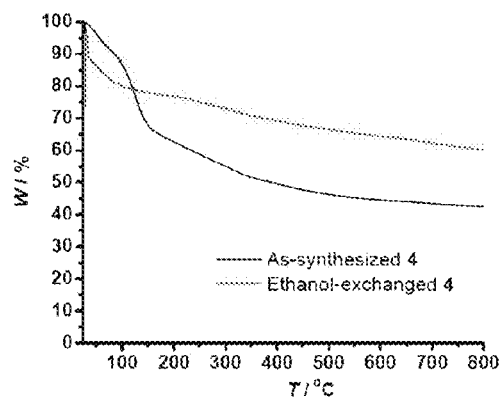
FIGS. 14A and 14B are graphs representing TGA plots of the as-synthesized and solvent-exchanged compounds 4-5.
Figure 14B:
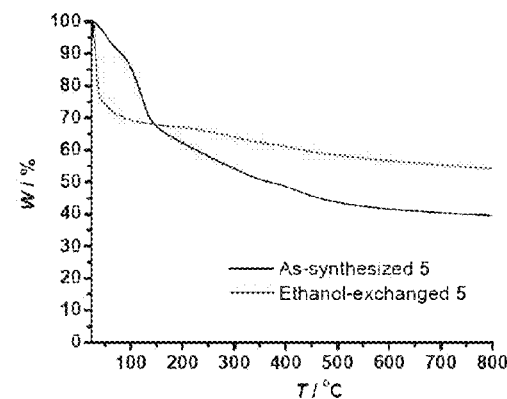
Figure 15A:
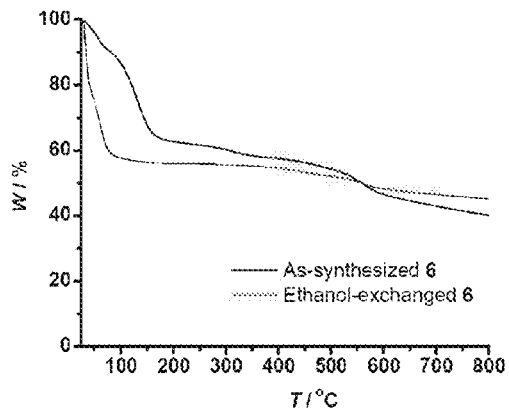
FIGS. 15A and 15B are graphs representing TGA plots of the as-synthesized and solvent-exchanged compounds 6-7.
Figure 15B:
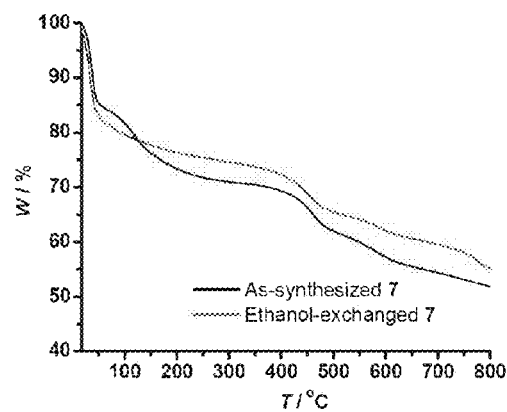
Figure 16:
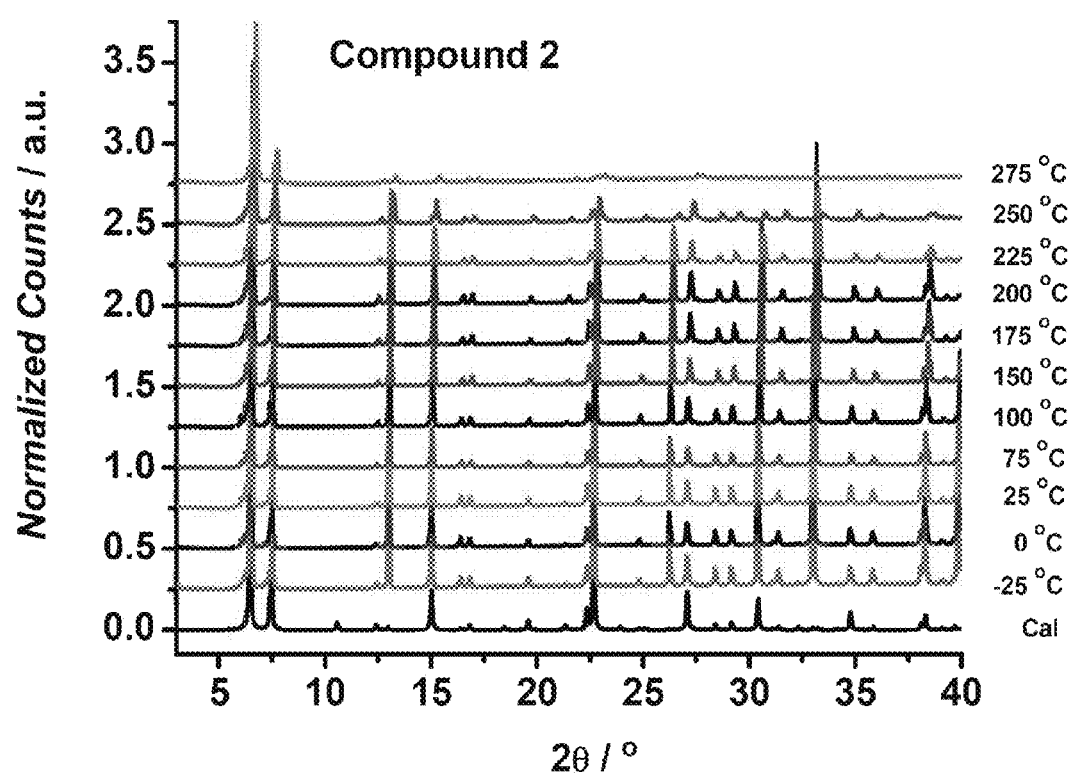
FIG. 16 is a graph representing variable-temperature (VT) PXRD of compound 2, revealing the thermal stability up to 275 degree C.
Figure 17:
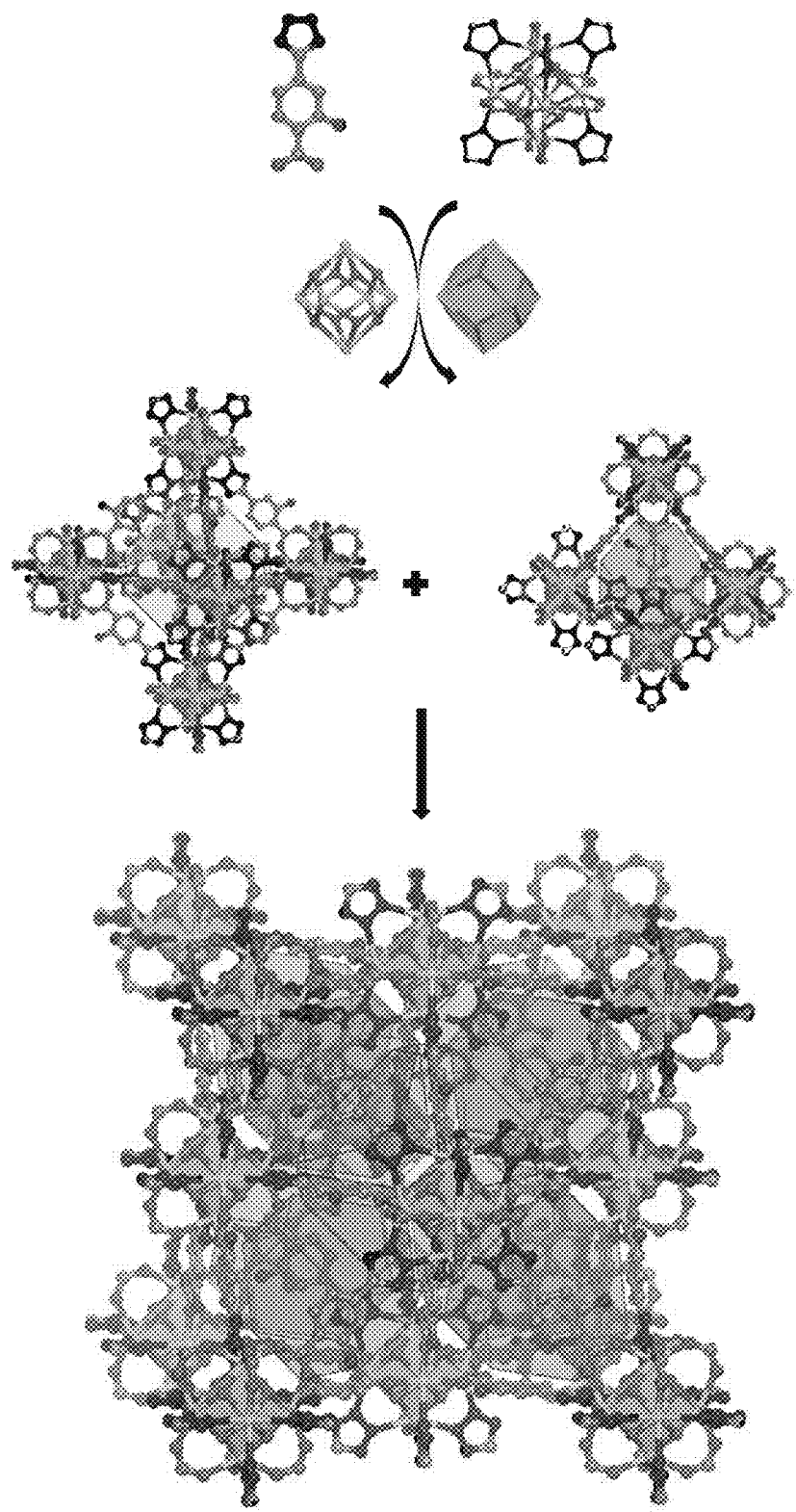
FIG. 17 is a ball-and-stick representation of compound 1, constructed from the assembly of 12-connected carboxylate/tetrazolate-based molecular building blocks (MBBs) linked together via a linear and heterofunctional FTZB organic linker, to give a 3-periodic fcu-MOF with two types of polyhedral cages: i.e. tetrahedral and octahedral.
Figure 18:
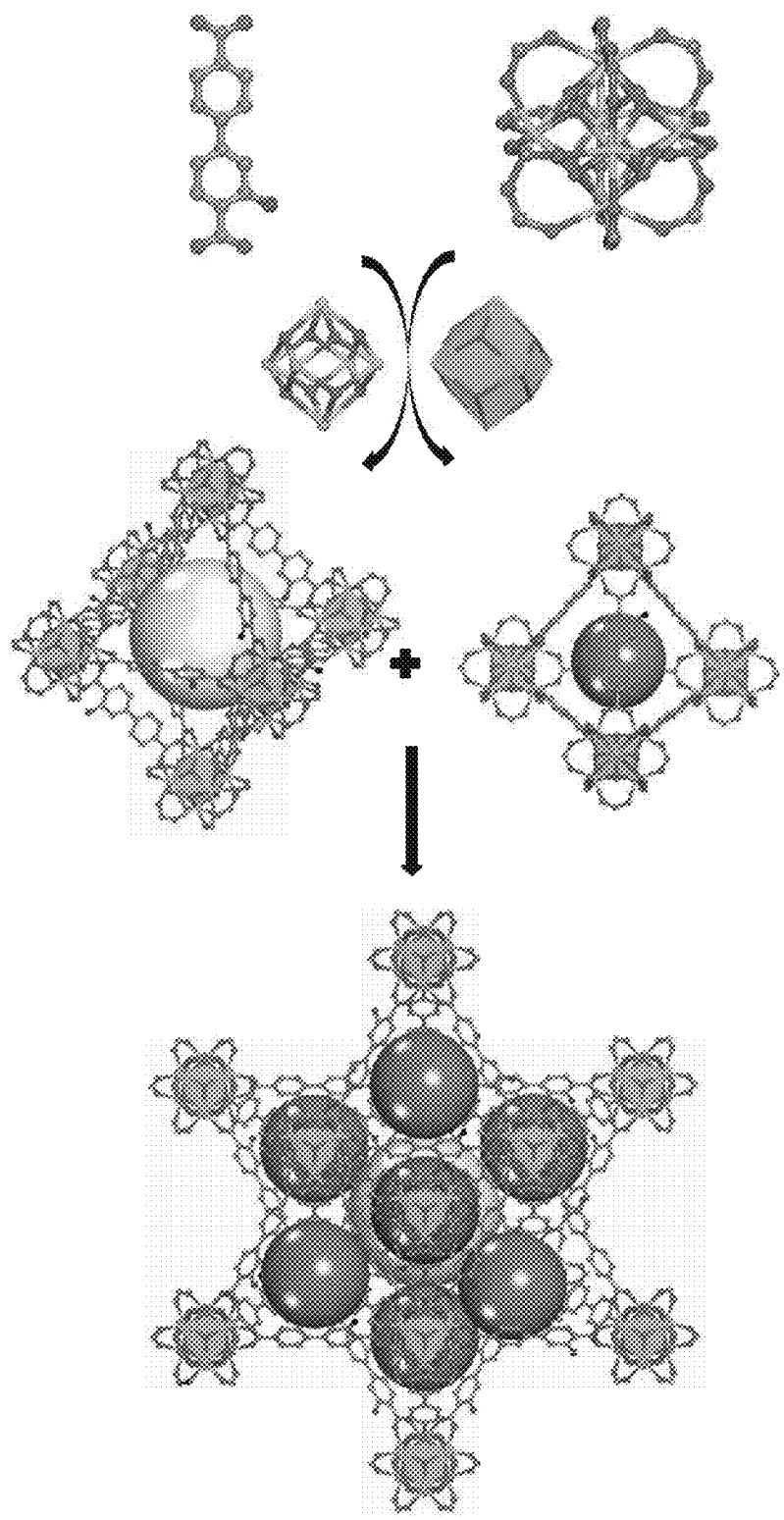
FIG. 18 is a ball-and-stick representation of compound 6, constructed from the assembly of 12-connected carboxylate-based MBBs linked together via a ditopic FBPDC organic linker, to give a 3-periodic fcu-MOF with two types of polyhedral cages.
Figure 19:
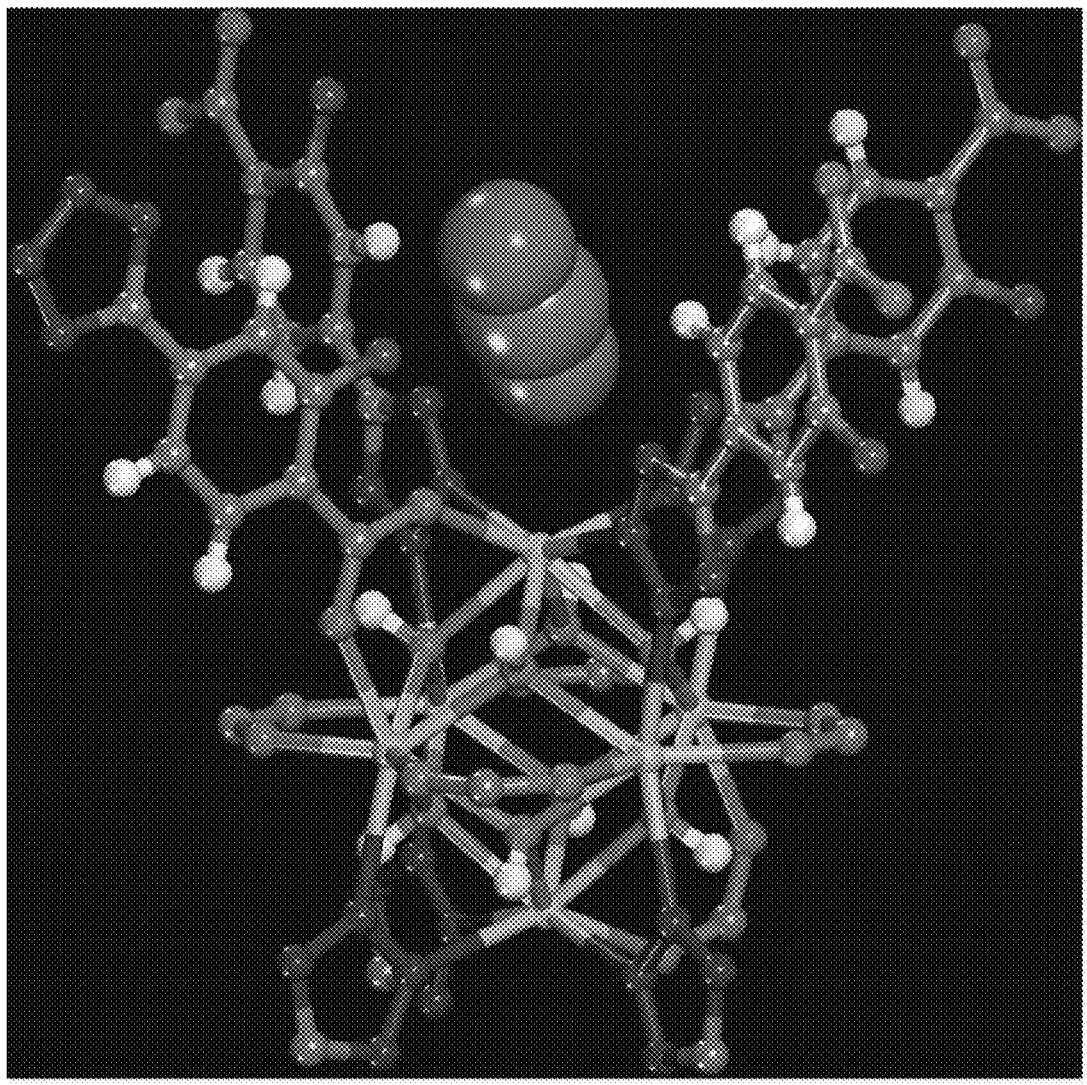
FIG. 19 is a synergetic effect representation of a $CO_2$ surrounded by an open metal site, uncoordinated nitrogen atoms of tetrazolate and polarizable fluoro atom as well as hydroxo moieties.

In order to achieve maximum and accurate sorption results, the phase purity of the porous material can first be verified. The phase purity of the bulk crystalline materials for 1 and 2 was independently confirmed by similarities between the calculated and as-synthesized powder X-ray diffraction (PXRD) patterns (FIGS. 6A and 6B). In addition, both compounds also show favorable water and thermal stability (FIGS. 2, 11 and 16), which is an important parameter for potential practical deployment of porous MOFs in carbon capture applications.

Figure 20:
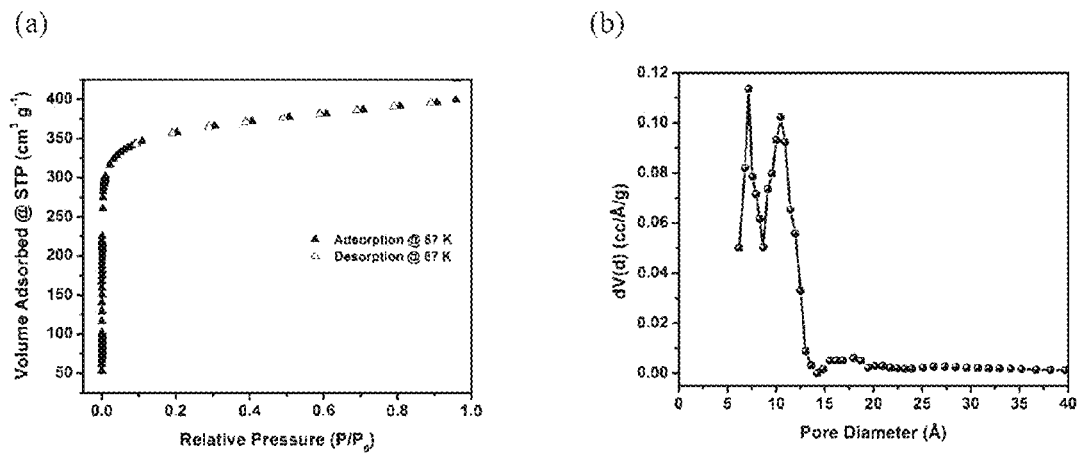
FIG. 20 are graphs representing Ar sorption isotherms collected at 87 K (a), pore size distribution analysis (b) for compound 1.
Figure 23:
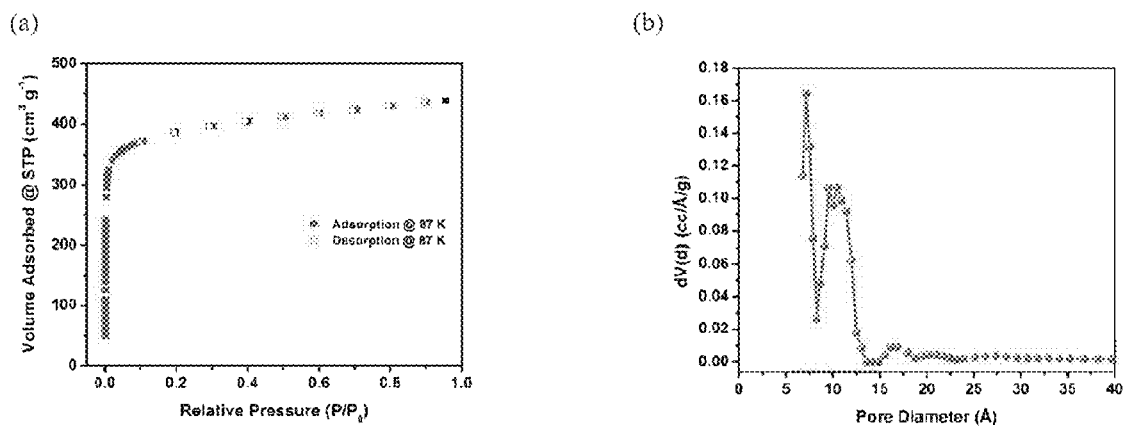

Argon gas adsorption studies performed on the methanol-exchanged samples show fully reversible type-I isotherms, representative of microporous materials (FIGS. 20 and 23). The apparent BET surface area and pore volume for 1 and 2 were estimated to be 1220 m$^2$ g$^{-1}$ and 0.51 cm$^3$ g$^{-1}$, and 1310 m$^2$ g$^{-1}$ and 0.56 cm$^3$ g$^{-1}$, respectively.

Figure 21:
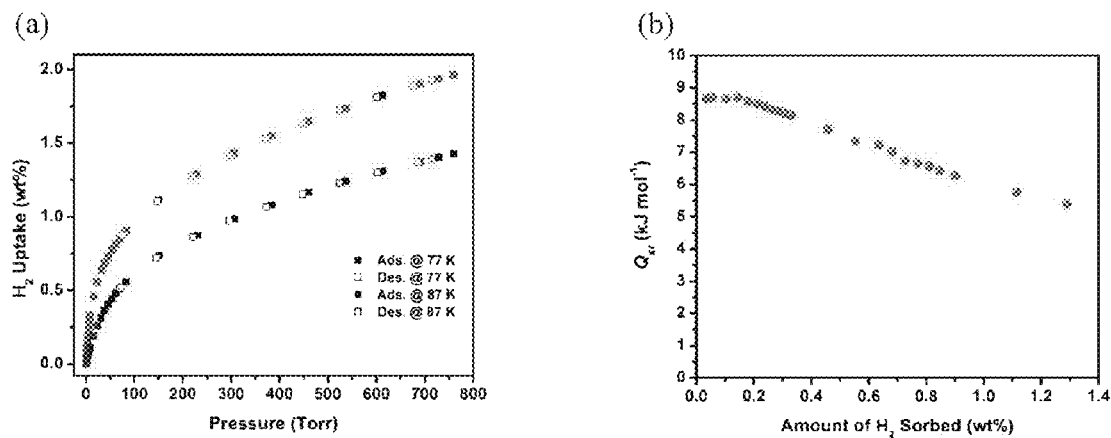
FIG. 21 are graphs representing $H_2$ sorption data for compound 1: (a) fully reversible $H_2$ isotherms collected at 77 and 87 K and (b) $Q_{st}$ for $H_2$ calculated from the corresponding isotherms.
Figure 22:
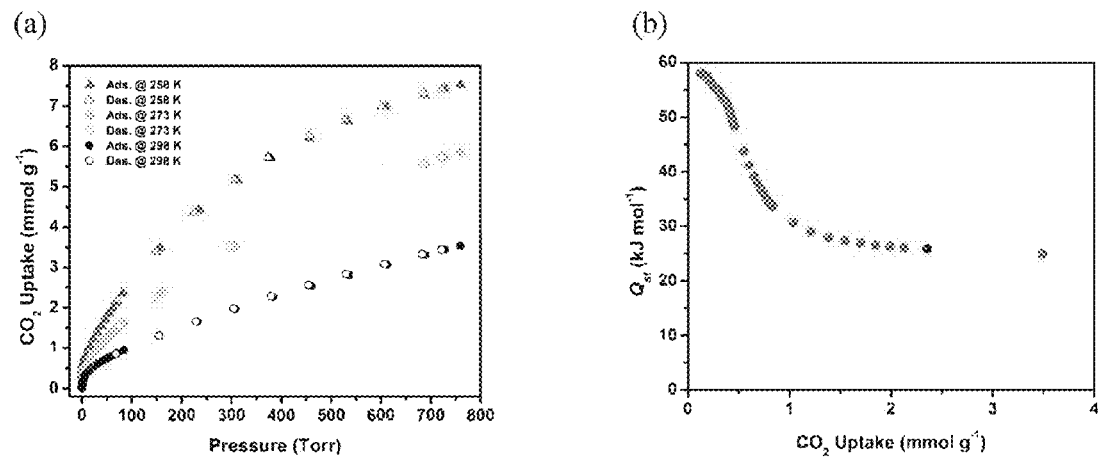
FIG. 22 are graphs representing $CO_2$ sorption data for compound 1: (a) fully reversible VT $CO_2$ isotherms and (b) $Q_{st}$ for $CO_2$ calculated from the corresponding isotherms FIG. 23 are graphs representing Ar sorption isotherms collected at 87 K (a), pore size distribution analysis (b) for compound 2.
Figure 24:
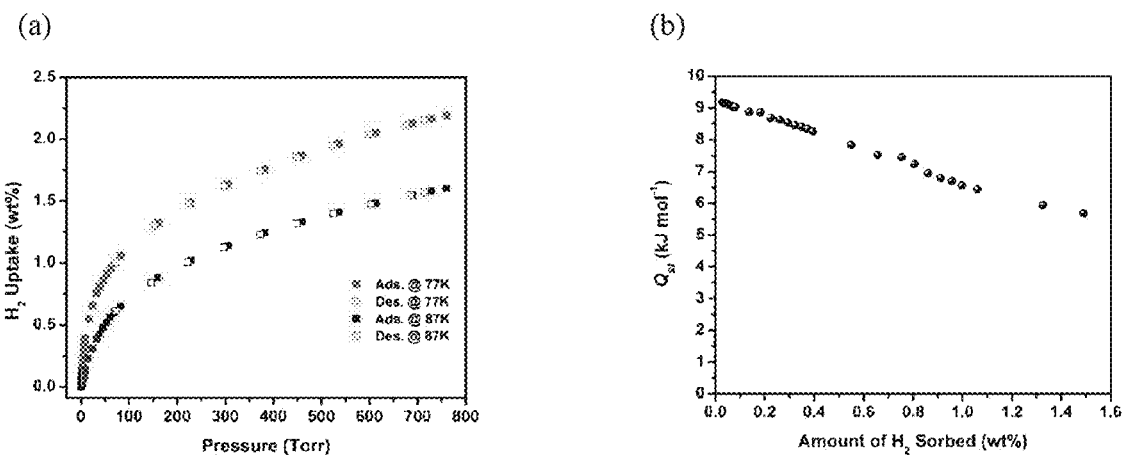
FIG. 24 are graphs representing $H_2$ sorption data for data for compound 2: (a) fully reversible $H_2$ isotherms collected at 77 and 87 K and (b) $Q_{st}$ for $H_2$ calculated from the corresponding isotherms.
Figure 25:
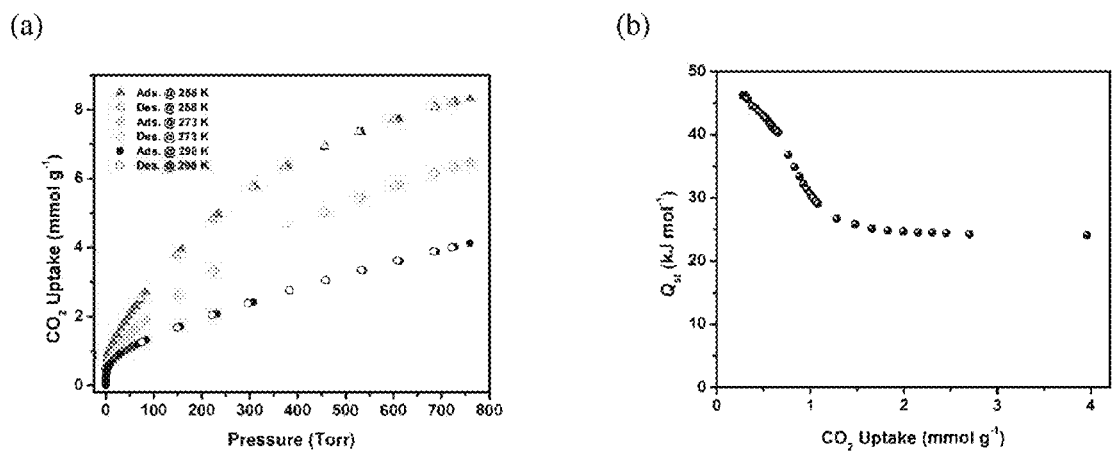
FIG. 25 are graphs representing $CO_2$ sorption data for compound 2: (a) fully reversible VT $CO_2$ isotherms and (b) $Q_{st}$ for $CO_2$ calculated from the corresponding isotherms.

In order to evaluate the performance of compounds 1 and 2, an initial H$_2$ adsorption study at low pressure was performed. The H$_2$ adsorption uptake was assessed to be 1.96 and 2.19 wt % at 760 torr and 77 K (FIG. 21(a) and S24(a)), while Q$_{st}$ for H$_2$ was determined and estimated to be 8.7 and 9.2 kJ mol$^{-1}$ at zero coverage for 1 and 2, respectively (FIGS. 21(b) and 24(b)).

Figure 3:
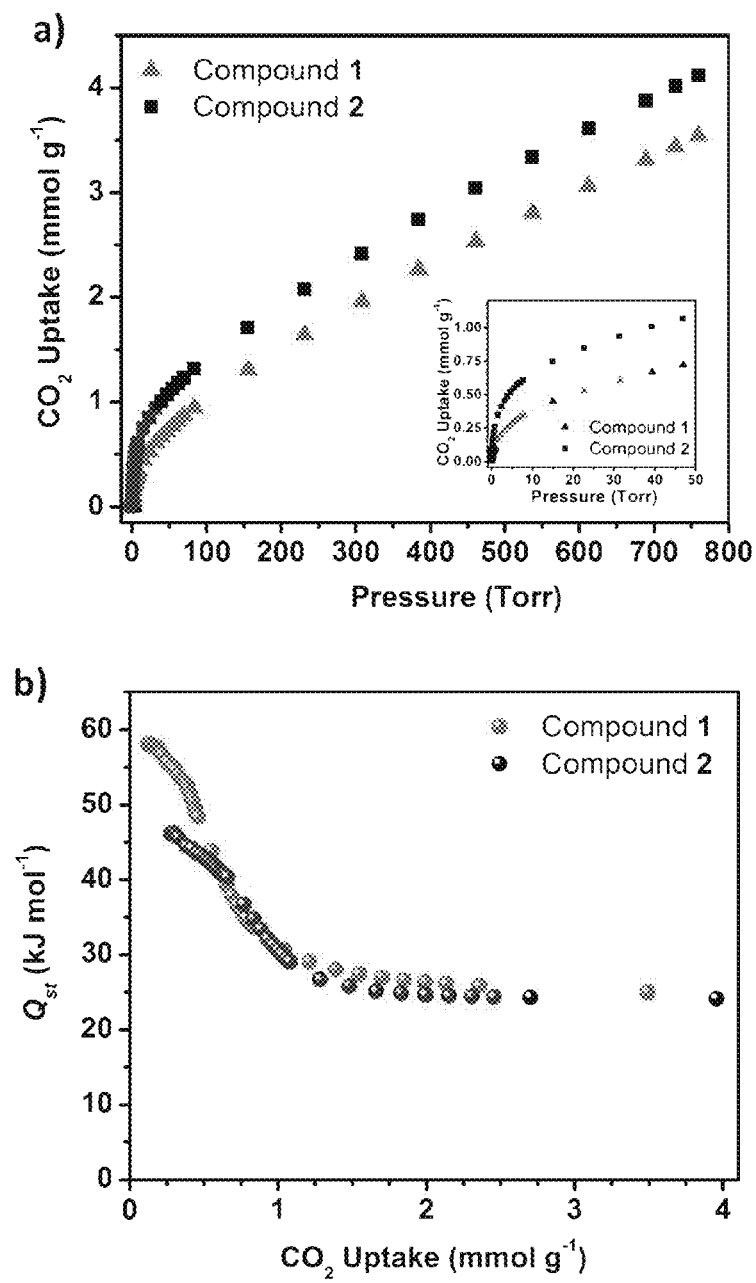
FIG. 3 are graphs representing (a) $CO_2$ data for 1 and 2 at 298 K and (b) $Q_{st}$ in 1 and 2 for $CO_2$ calculated from the 258, 273 and 298 K isotherms.
Figure 4:
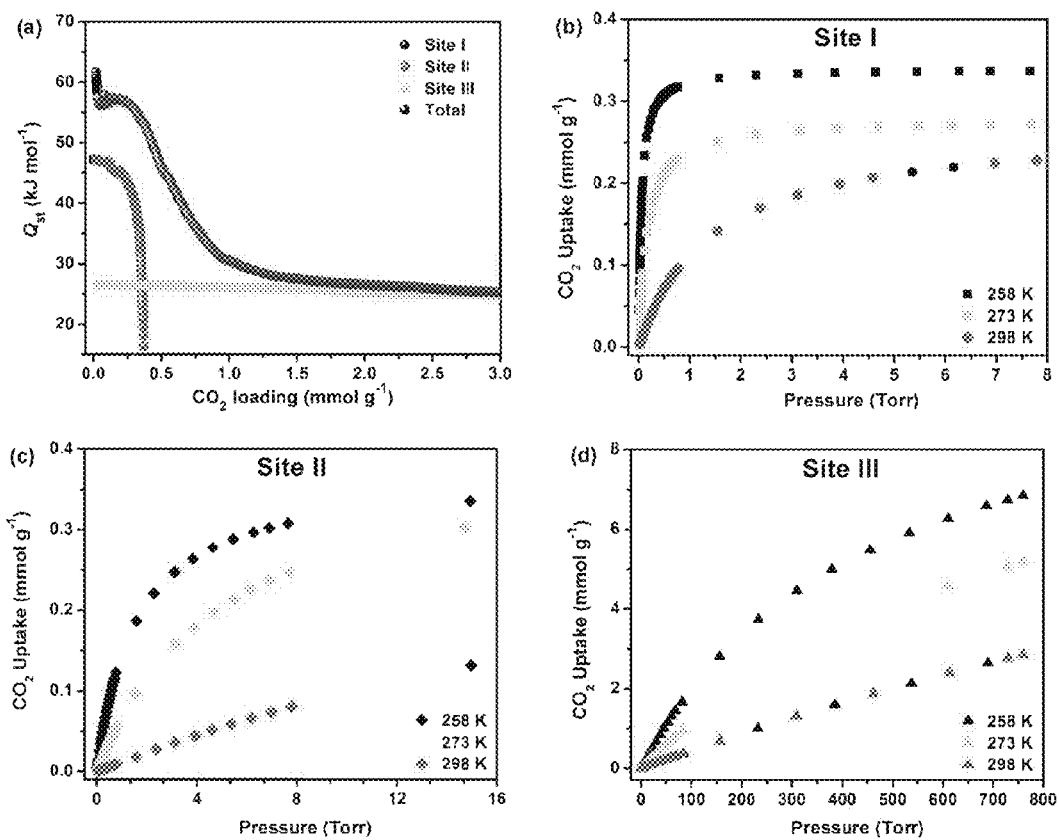
FIG. 4 are graphs representing (a) $Q_{st}$ for $CO_2$ of compound 1 in sites I, II, and III compared to the total $Q_{st}$ as determined by the TSL model and $CO_2$ adsorption isotherms of compound 1 for sites I (b), II (c), and III (d) using the TSL model.
Figure 26:
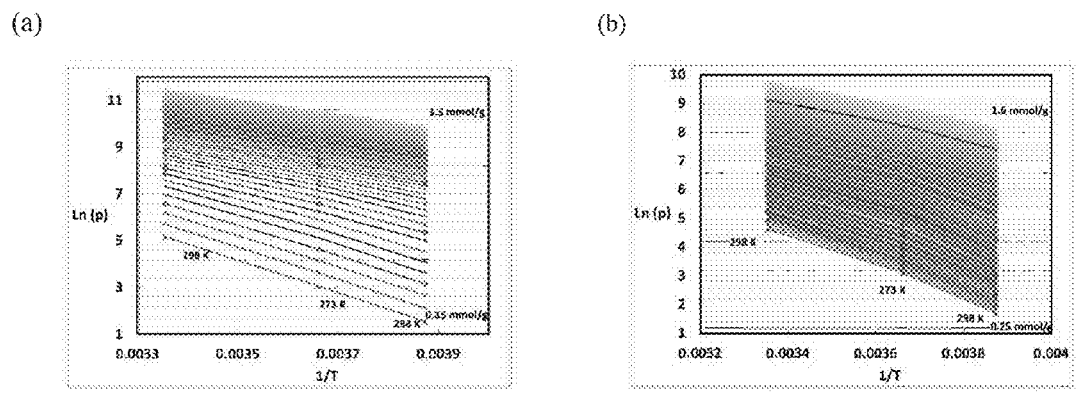
FIG. 26 are graphs representing $CO_2$ adsorption isosters for compounds 1 (a) and 2 (b), confirming the accuracy of the $Q_{st}$ determined from VT $CO_2$ adsorption isotherms as evidenced by the linearity in the isosters.
Figure 54:
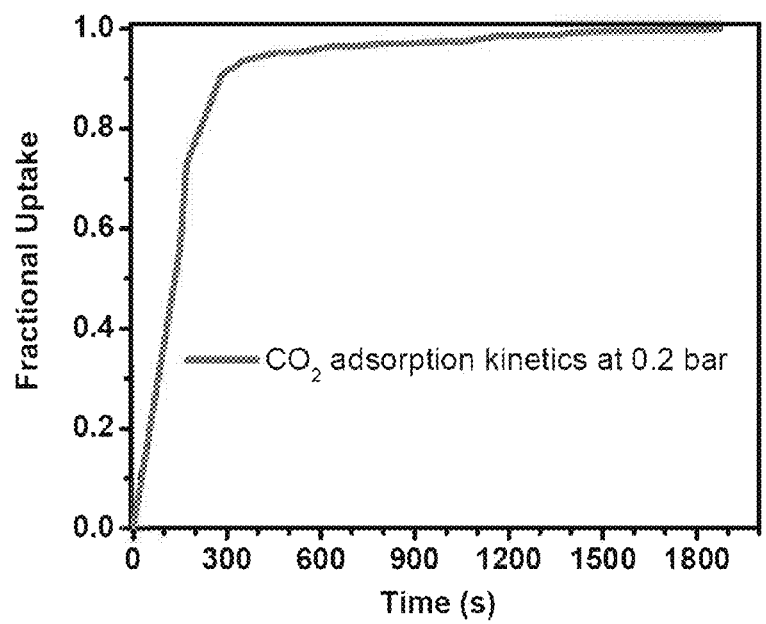
FIG. 54 is a graph representing $CO_2$ adsorption kinetics curve for compound 2 at 0.2 bar and 298 K (collected during adsorption measurements).

To further this study, the CO$_2$ sorption was investigated, and it was found that 1 and 2 reversibly adsorb a significant amount of CO$_2$ under ambient conditions, i.e., 3.5 mmol g$^{-1}$ (15.6%) and 4.1 mmol g$^{-1}$(18.1%), respectively, at 298 K and 760 torr (FIG. 3(a)). Interestingly and in contrast to most MOFs, a steep slope is observed in the low pressure region for both materials, a feature that is indicative of enhanced CO$_2$-MOF interactions. Indeed, the Q$_{st}$ for CO$_2$ calculated from the corresponding variable temperature adsorption isotherms was 58.1 and 46.2 kJ mol$^{-1}$, for 1 and 2, respectively, at low loading (FIG. 3(b)). In fact, these results are discerned as amongst the highest reported thus far for fully reversible CO$_2$ sorption on MOFs in the absence of any post-synthetic modification and/or surface area reduction. The accuracy of the Q$_{st}$ determination was confirmed across the entire loading range by verifying the linearity of CO$_2$ adsorption isosters (FIG. 26). At the exception of Mg-MOF-74, the CO$_2$ uptake at low pressure (0.01 bar and 298 K) for 1 and 2 (Table 1) is the highest reported thus far for MOFs (including amine-functionalized MOFs) with relatively fast CO$_2$ adsorption kinetics (FIG. 54).

TABLE 1

CO$_2$ uptake in compounds 1 and 2 as compared to other MOFs reported in the literature.

| MOFs | CO$_2$ uptake at 0.01 bar (mmol g$^{-1}$) | Q$_{st}$ at low coverage (kJ mol$^{-1}$) |
|---|---|---|
| Compound 1 | 0.33 | 58.1 |
| Compound 2 | 0.62 | 46.2 |
| Mg-MOF-74[a] | 1.5 | 47 |
| Mmen-Cu BTTri[b] | 0.023 | 96 |

[a]Mg-MOF-74: Caskey, S. R.; Wong-Foy, A. G.; Matzger, A. J. *J. Am. Chem. Soc.* 2008, 130, 10870-10871.
[b]Mmen-Cu BTTri: McDonald, T. M.; D'Alessandro, D. M.; Krishna, R.; Long, J. R. *Chem. Sci.* 2011, 2, 2022-2028.

Figure 5:
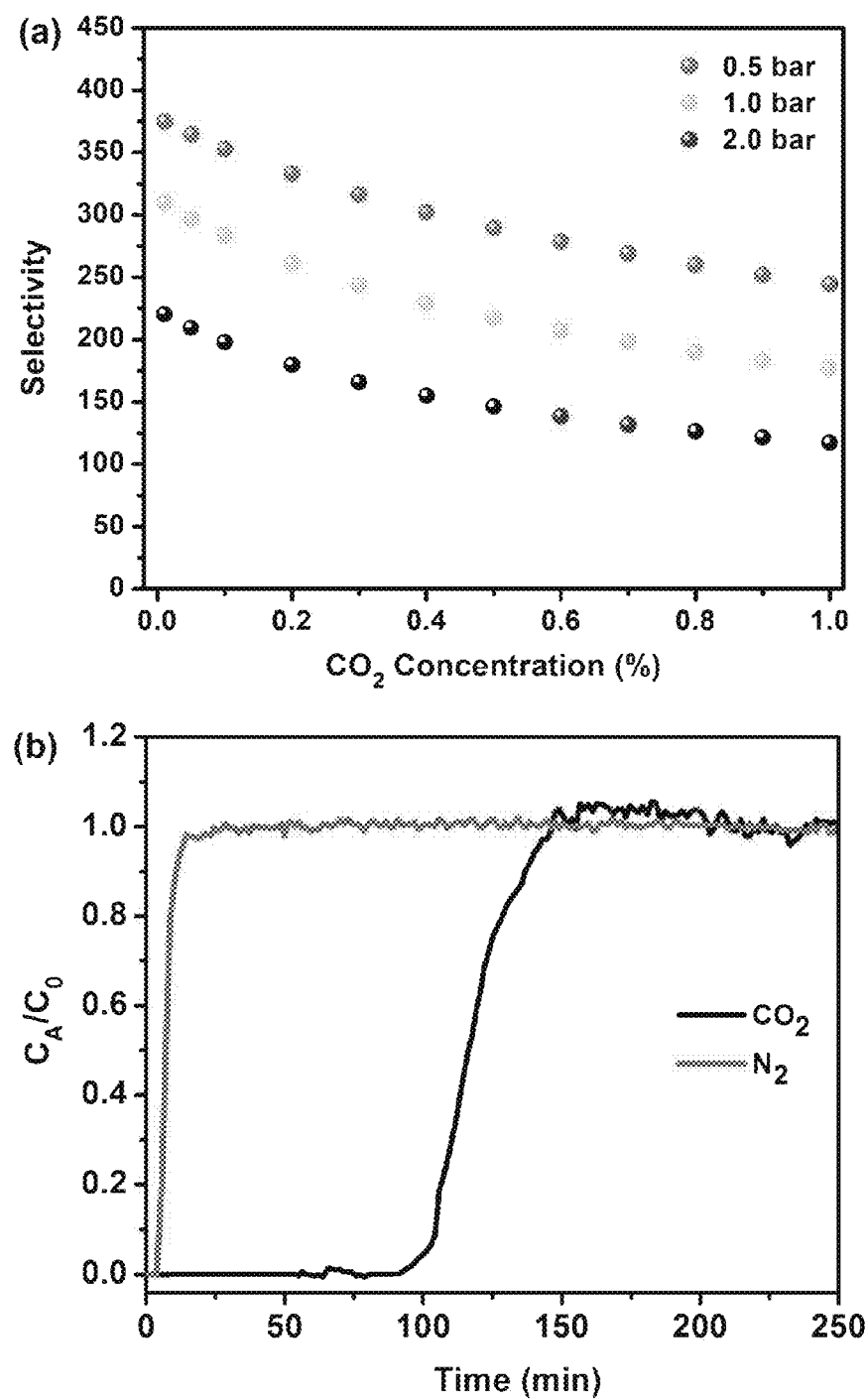
FIG. 5 are graphs representing (a) $CO_2$ selectivity over $N_2$ resulted from the interaction with site I at 298 K at different total pressures in 0.5-2.0 bar range calculated using IAST for compound 1 and (b) experimental breakthrough test of traces (1000 ppm) $CO_2$ in mixture with $N_2$ on compound 1.
Figure 27:
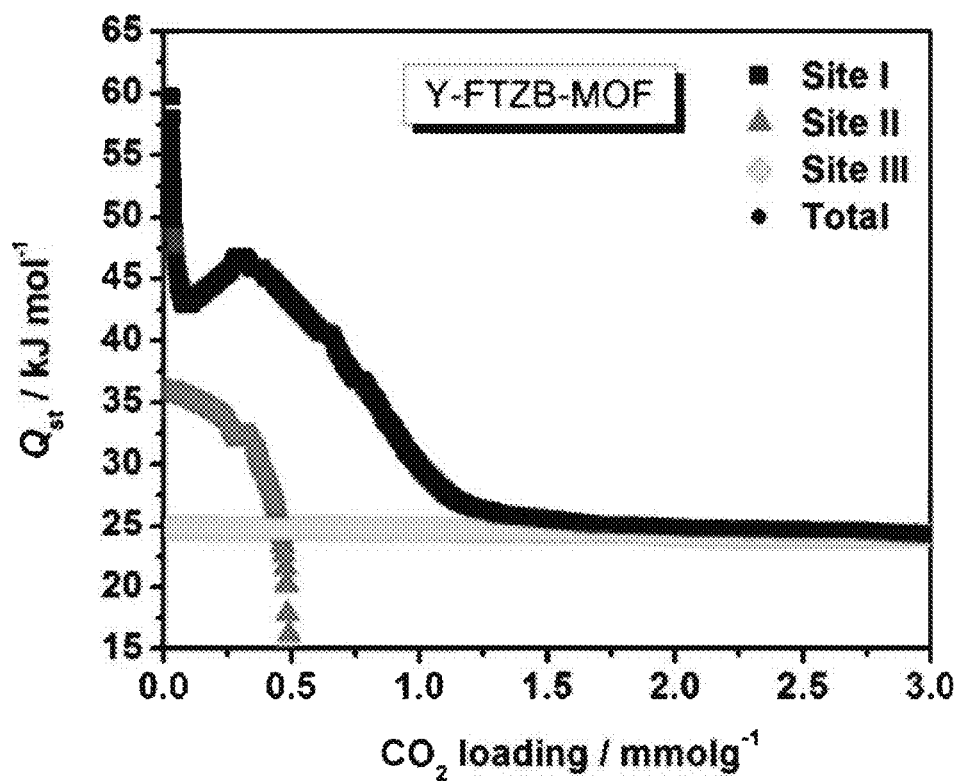
FIG. 27 is a graph representing $Q_{st}$ for $CO_2$ of compound 2 in sites I, II and III compared to the total $Q_{st}$ as determined by the TSL model.
Figure 28A:
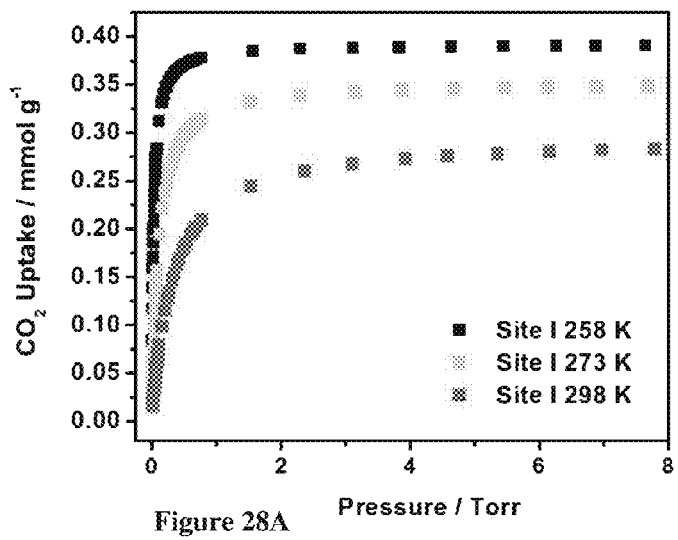
FIGS. 28A-28C are graphs representing $CO_2$ adsorption isotherms of compound 2 for sites I, II and III using the TSL model.
Figure 28B:
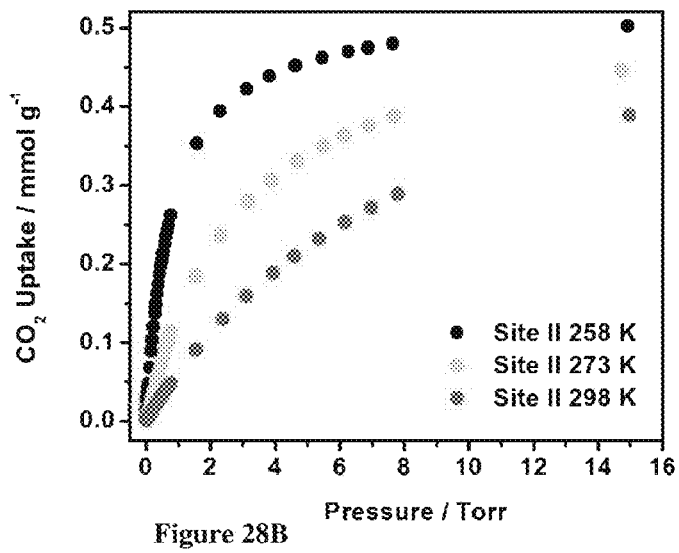
Figure 28C:
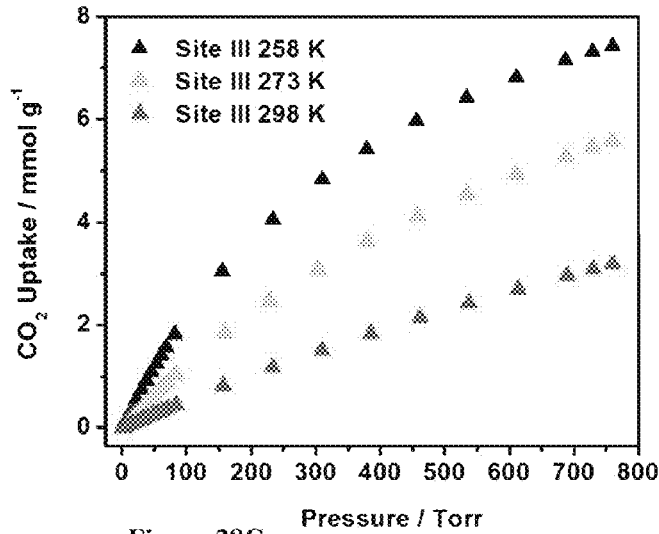
Figure 29:
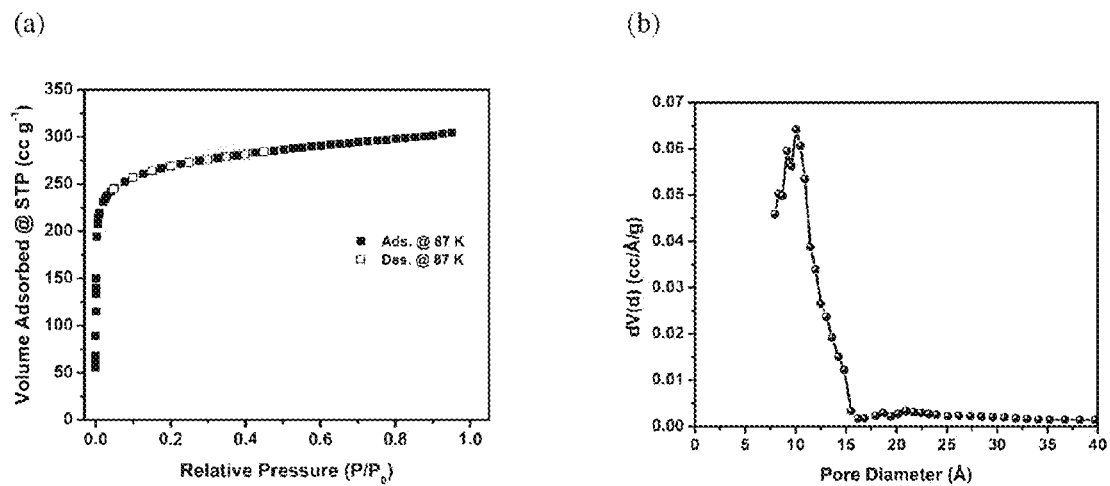
FIG. 29 are graphs representing Ar sorption isotherms collected at 87 K (a), pore size distribution analysis (b) for compound 3.
Figure 30:
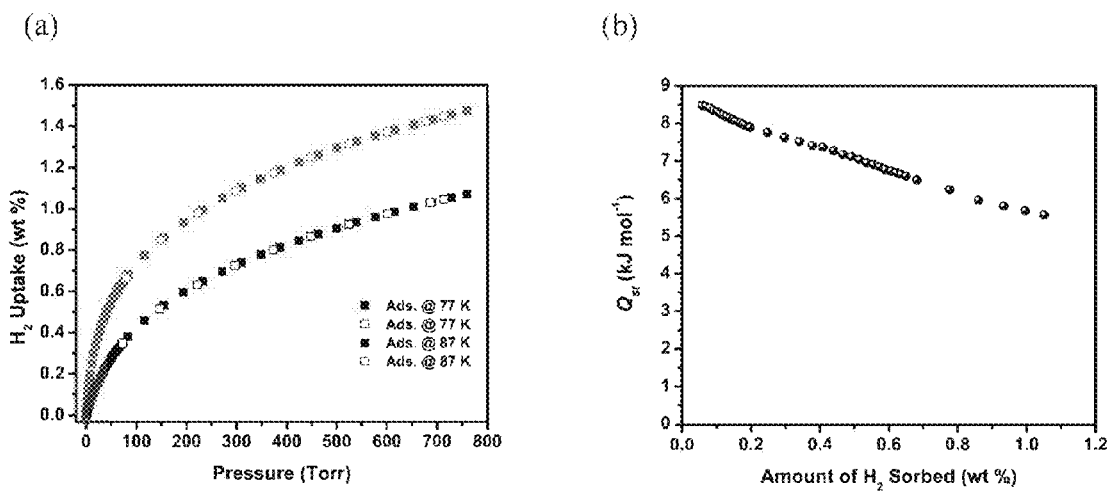
FIG. 30 are graphs representing $H_2$ sorption data for data for compound 3: (a) fully reversible $H_2$ isotherms collected at 77 and 87 K and (b) $Q_{st}$ for $H_2$ calculated from the corresponding isotherms.
Figure 31:
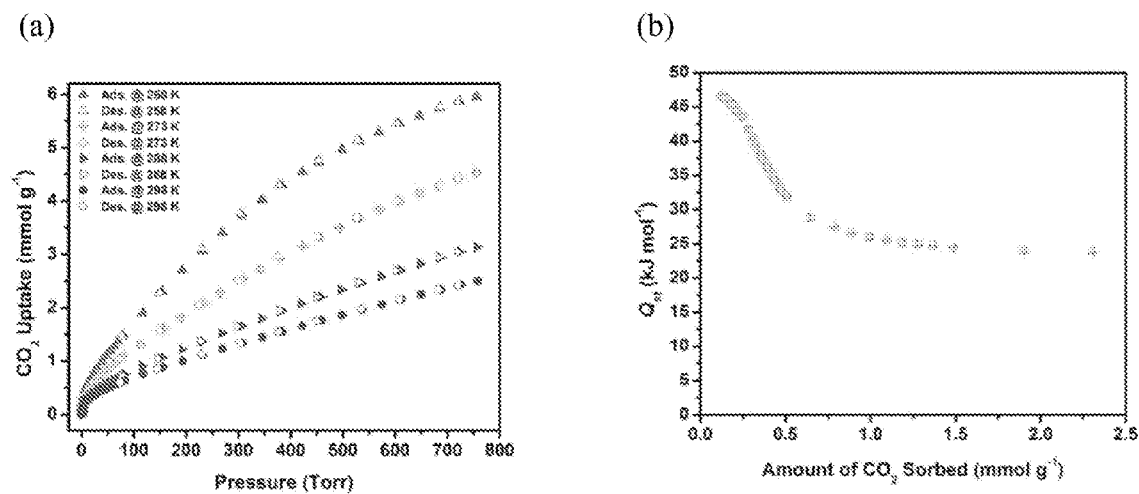
FIG. 31 are graphs representing $CO_2$ sorption data for compound 3: (a) fully reversible VT $CO_2$ isotherms and (b) $Q_{st}$ for $CO_2$ calculated from the corresponding isotherms.
Figure 32:
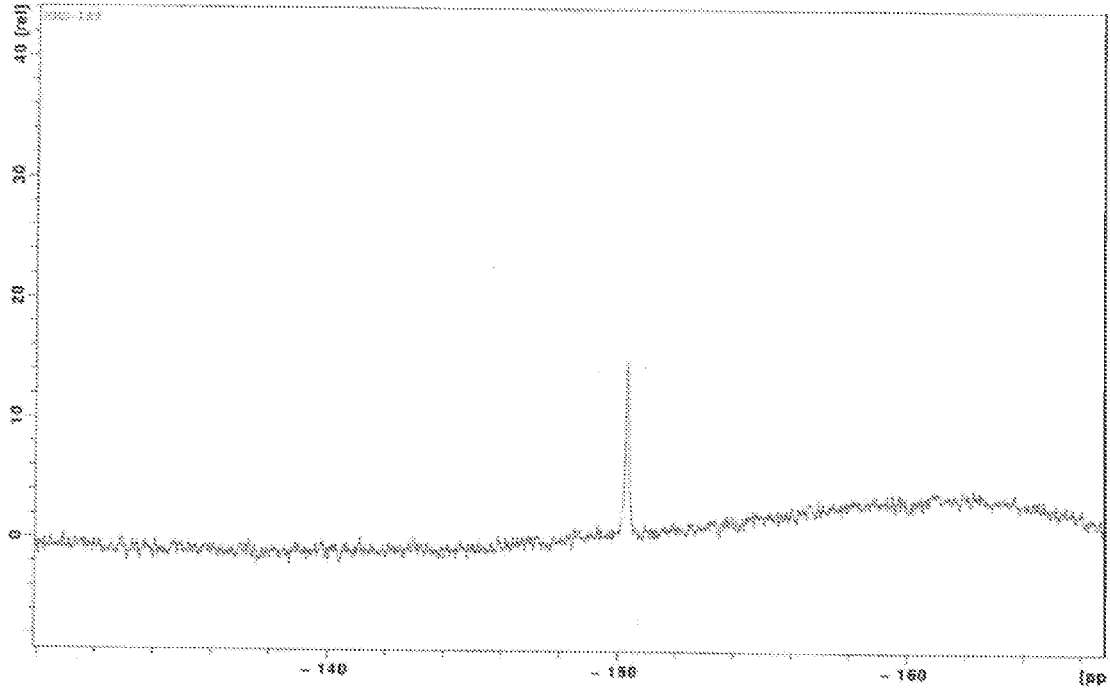
FIG. 32 is a graph representing $^{19}F$ NMR spectrum of compound 3 digested in HCl and DMSO, showing the presence of the modulator, 2-fluorobenzoic acid, and thus resulting in a reduced pore volume compared to the theoretical SCXRD data (i.e. 0.39 vs 0.55 $cm^3\,g^{-1}$).
Figure 33:
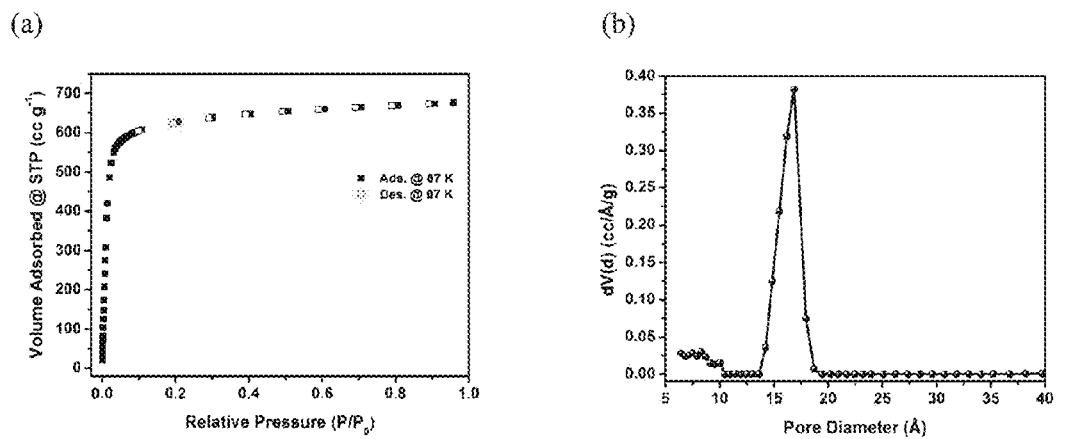
FIG. 33 are graphs representing Ar sorption isotherms collected at 87 K (a), pore size distribution analysis (b) for compound 4.
Figure 34:
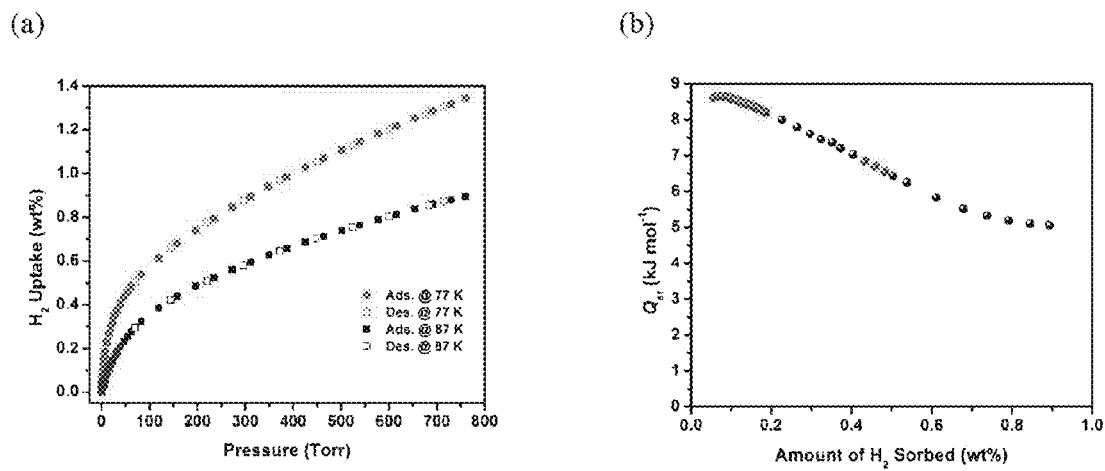
FIG. 34 are graphs representing $H_2$ sorption data for compound 4: (a) fully reversible $H_2$ isotherms collected at 77 and 87 K and (b) $Q_{st}$ for $H_2$ calculated from the corresponding isotherms.
Figure 35:
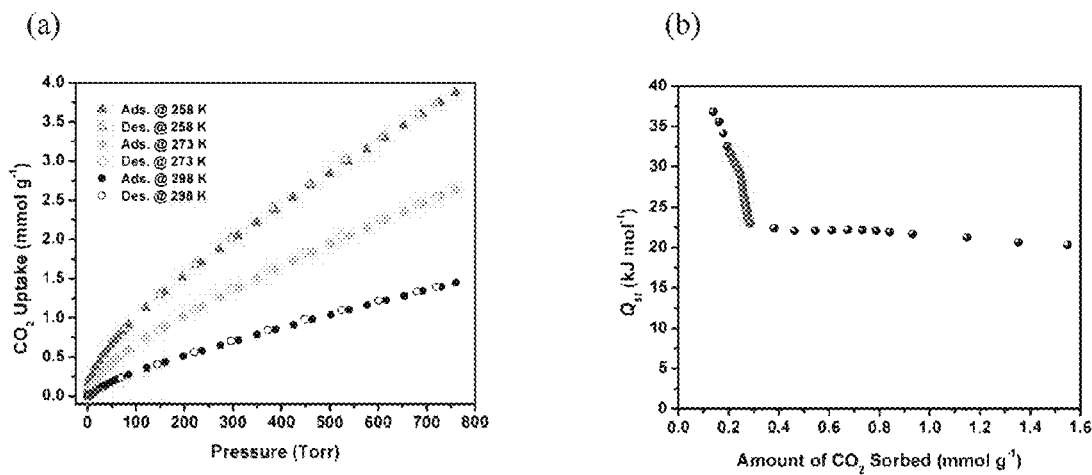
FIG. 35 are graphs representing $CO_2$ sorption data for compound 4: (a) fully reversible VT $CO_2$ isotherms and (b) $Q_{st}$ for $CO_2$ calculated from the corresponding isotherms.
Figure 36:
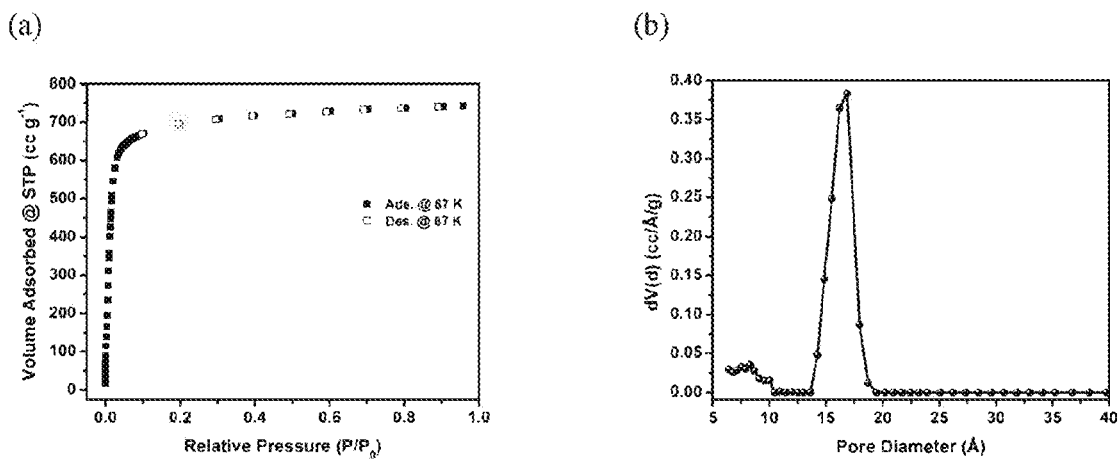
FIG. 36 are graphs representing Ar sorption isotherms collected at 87 K (a) and pore size distribution analysis (b) for compound 5.
Figure 37:
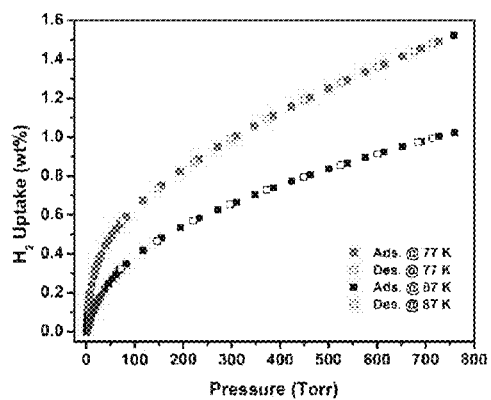
FIG. 37 are graphs representing $H_2$ sorption data for compound 5: (a) fully reversible $H_2$ isotherms collected at 77 and 87 K and (b) $Q_{st}$ for $H_2$ calculated from the corresponding isotherms.
Figure 37:
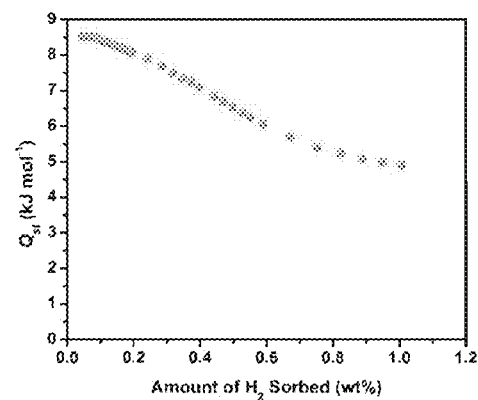
Figure 38:
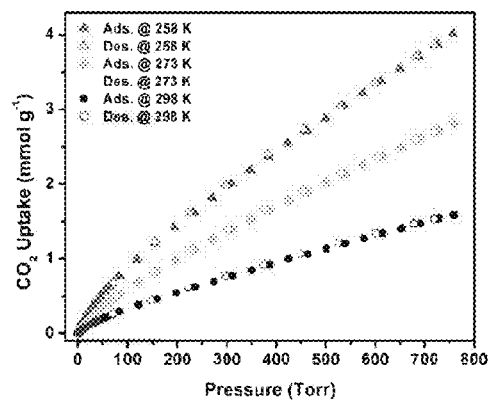
FIG. 38 are graphs representing $CO_2$ sorption data for compound 5: (a) fully reversible VT $CO_2$ isotherms and (b) $Q_{st}$ for $CO_2$ calculated from the corresponding isotherms FIG. 39 are graphs representing Ar sorption isotherms collected at 87 K (a), pore size distribution analysis (b) for compound 6.
Figure 38:
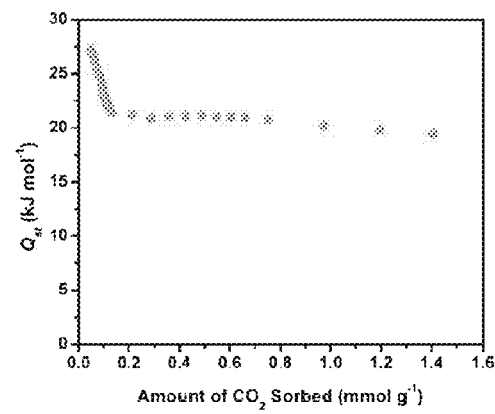
Figure 39:
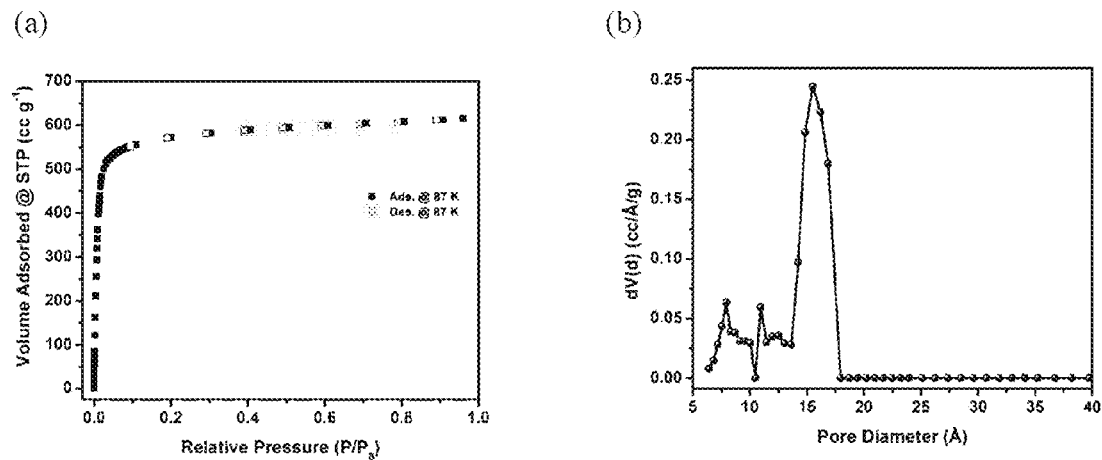
Figure 40:
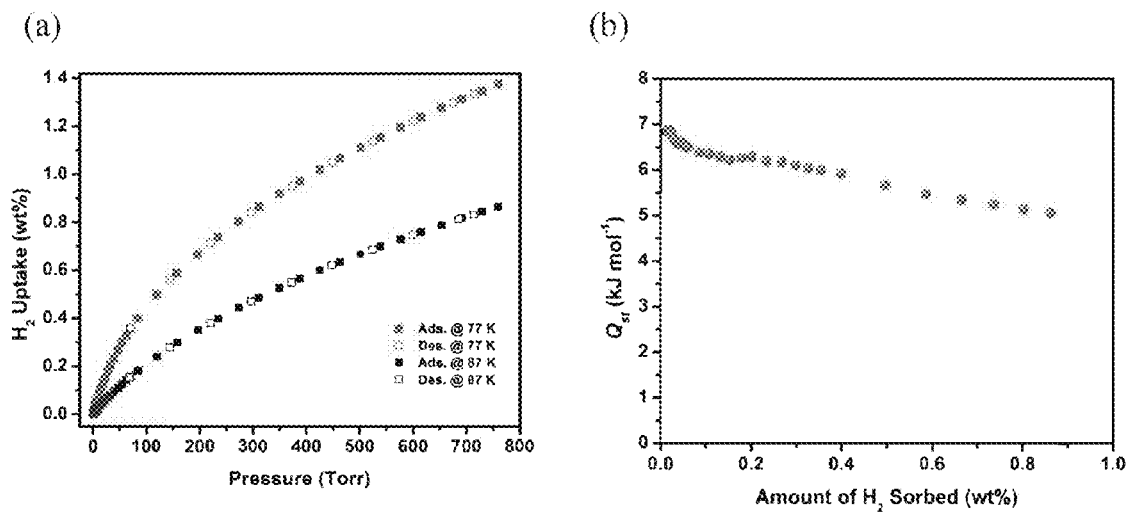
FIG. 40 are graphs representing $H_2$ sorption data for compound 6: (a) fully reversible $H_2$ isotherms collected at 77 and 87 K and (b) $Q_{st}$ for $H_2$ calculated from the corresponding isotherms.
Figure 41:
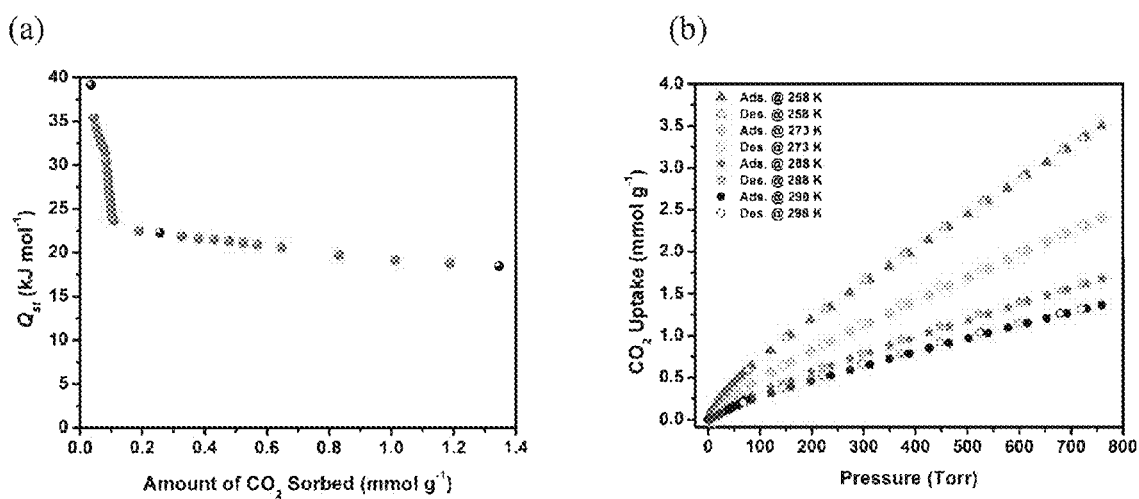
FIG. 41 are graphs representing $CO_2$ sorption data for compound 6: (a) fully reversible VT $CO_2$ isotherms and (b) $Q_{st}$ for $CO_2$ calculated from the corresponding isotherms.
Figure 42:
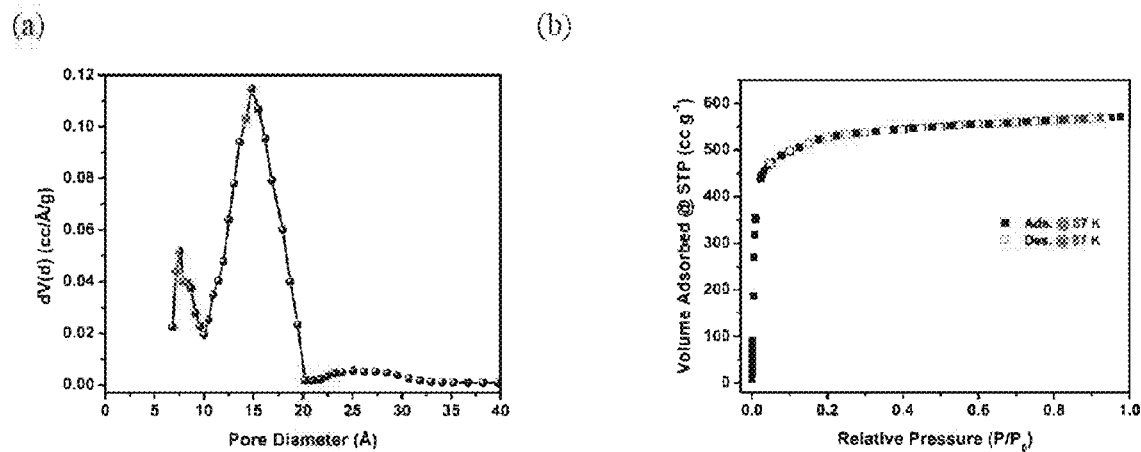
FIG. 42 are graphs representing Ar sorption isotherms collected at 87 K (a), pore size distribution analysis (b) for compound 7.
Figure 43:
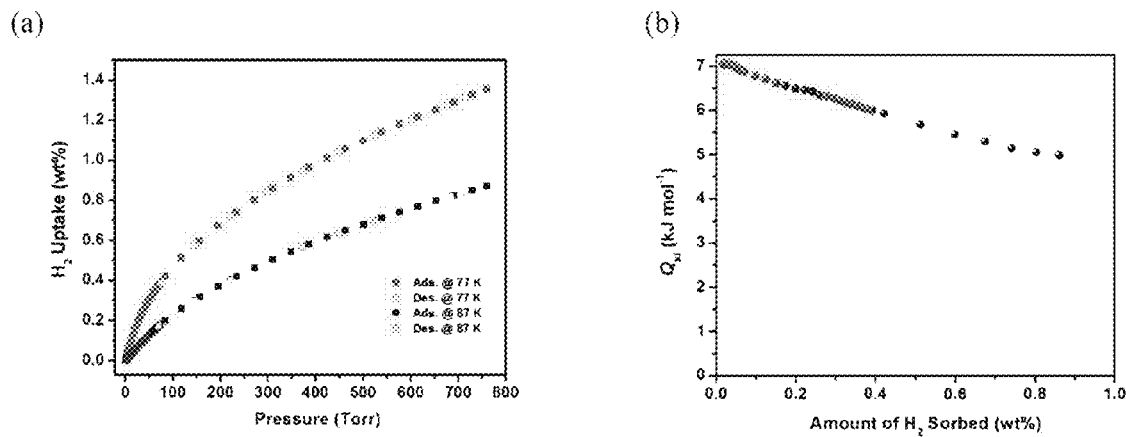
FIG. 43 are graphs representing $H_2$ sorption data for compound 7: (a) fully reversible $H_2$ isotherms collected at 77 and 87 K and (b) $Q_{st}$ for $H_2$ calculated from the corresponding isotherms.
Figure 44:
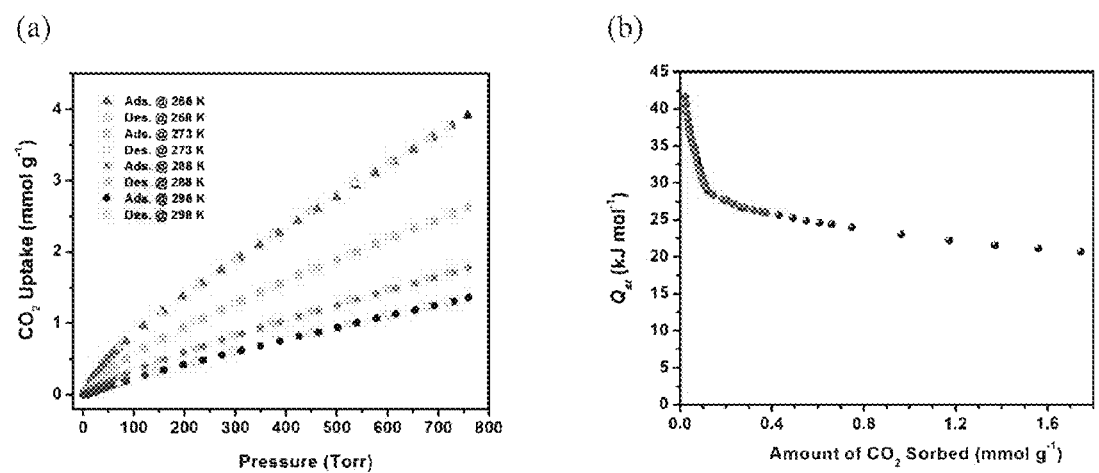
FIG. 44 are graphs representing $CO_2$ sorption data for compound 7: (a) fully reversible VT $CO_2$ isotherms and (b) $Q_{st}$ for $CO_2$ calculated from the corresponding isotherms.
Figure 45:
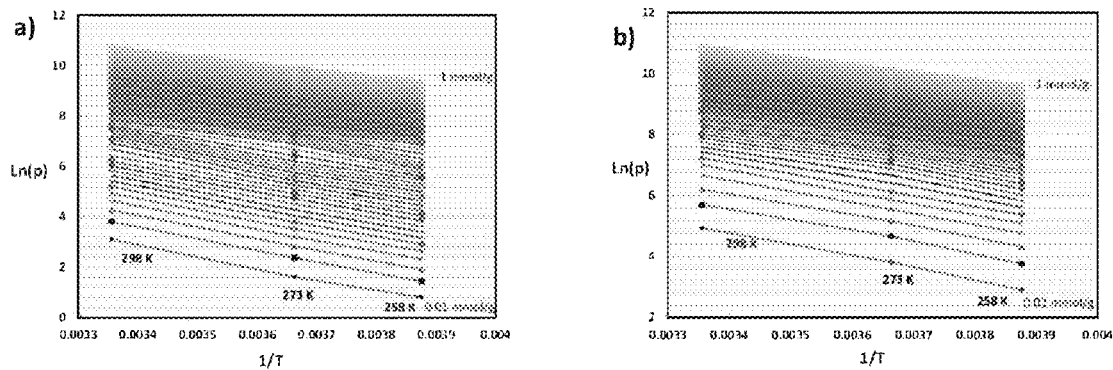
FIG. 45 are graphs representing $CO_2$ adsorption isosters for compounds 4 (a) and 5 (b).
Figure 46:
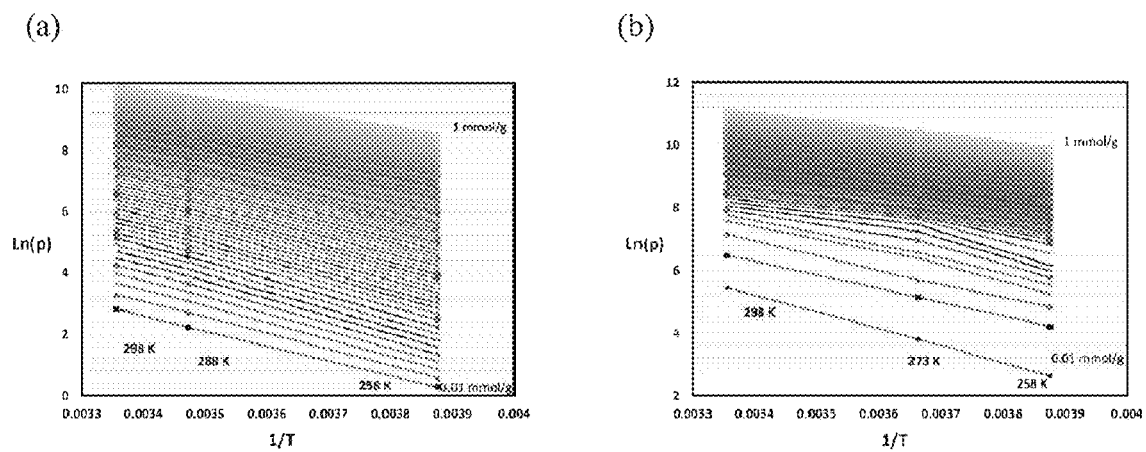
FIG. 46 are graphs representing $CO_2$ adsorption isosters for compounds 3 (a) and 6 (b).
Figure 47:
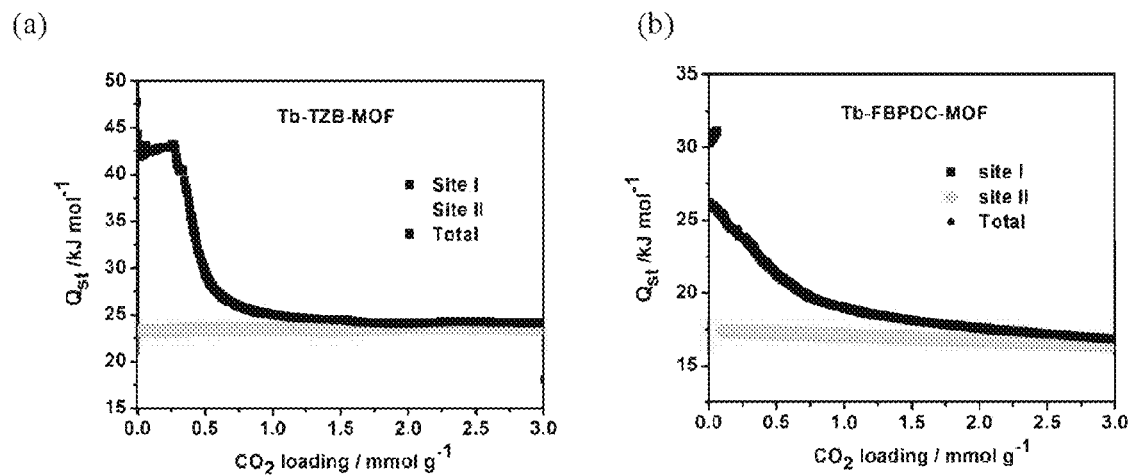
FIG. 47 are graphs representing $Q_{st}$ for $CO_2$ of compounds 3 (a) and 6 (b) in sites I and II compared to the total $Q_{st}$ as determined by the DSL model.
Figure 57:
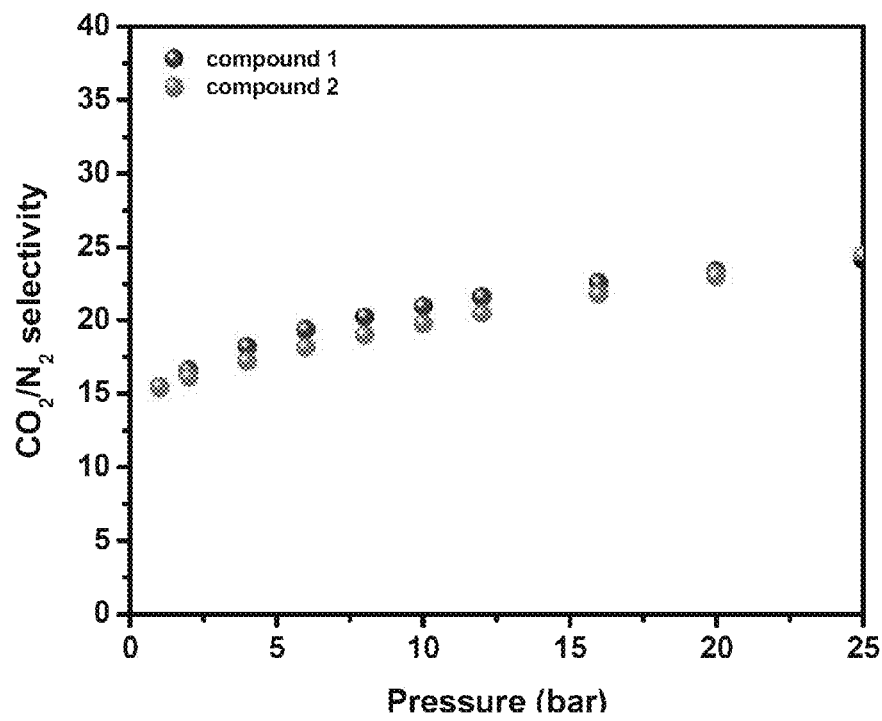
FIG. 57 is a graph representing $CO_2$ over $N_2$ selectivity for compound 1 and 2 calculated using IAST for $CO_2/N_2$: 10/90 gas mixture at 298 K.

In order to pinpoint and understand the different energetic levels associated with the unique CO$_2$ adsorption properties observed in 1 and 2, particularly at low pressures, we performed an in-depth Q$_{st}$ analysis study using a multiple site Langmuir model (MSL). In fact, three energetic sites were clearly identified and derived from the best fit and convergence obtained when using the triple site Langmuir model (FIG. 27). The observed energies for sites I and III were found to be identical in 1 and 2, ca. 60 and 25-26 kJ mol$^{-1}$, respectively. The former energetic site can be attributed to the localized high concentration of charge density resultant from the mutual presence of both a fluoro substituent and the nitrogen-rich tetrazolate moiety in proximal vicinity of the open metal site, while site III is simply due to the effect of pore filling. See, for example, Sumida, K.; Rogow, D. L.; Mason, J. A.; McDonald, T. M.; Bloch, E. D.; Herm, Z. R.; Bae, T.-H.; Long, J. R. *Chem. Rev.* 2012, 112, 724-781; Lin, J.-B.; Zhang, J.-P.; Chen, X.-M. *J. Am. Chem. Soc.* 2010, 132, 6654-6656; Lin, Q.; Wu, T.; Zheng, S.-T.; Bu, X.; Feng, P. *J. Am. Chem. Soc.* 2012, 134, 784-787; Burd, S. D.; Ma, S. Q.; Perman, J. A.; Sikora, B. J.; Snurr, R. Q.; Thallapally, P. K.; Tian, J.; Wojtas, L.; Zaworotko, M. J. *J. Am. Chem. Soc.* 2012, 134, 3663-3666; Luebke, R.; Eubank, J. F.; Cairns, A. J.; Belmabkhout, Y.; Wojtas, L.; Eddaoudi, M. *Chem. Commun.*, 2012, 48, 1455-1457, each of which is incorporated by reference in its entirety. Differences arising from the choice of metal ion are evident in site II, where energetic levels of 47 and 35 kJ mol$^{-1}$ were determined for compounds 1 and 2, respectively. The recorded $Q_{st}$ is likely the average energy of these sites, while the total $CO_2$ uptake is the summation of adsorption isotherms for sites I, II and III (FIGS. 4B-4D and 28A-28C). The presence of conical pockets (i.e., tripodal and quadrapodal narrow size cavities), decorated with fluoro moieties and tetrazolate groups, can create a high localized charge density and promote synergetic effects favorable for enhanced $CO_2$ sorption at low loadings. Using site I parameters for compound 1, ideal adsorbed solution theory (IAST; see Myers, A. L. & Prausnitz, J. M. AlChE J. 11, 1965, 121-127, which is incorporated by reference in its entirety) prediction of adsorption at various trace concentration of $CO_2$ (from 100 ppm to 1%) in a mixture with $N_2$, mimicking vacuum swing operational mode at various working pressures, revealed an exceptionally high adsorption selectivity (ca. 370) for $CO_2$ over $N_2$ (FIG. 5A). This finding was further confirmed experimentally using a column breakthrough test with a $CO_2/N_2$:0.01/99.99% mixture (FIG. 57), showing an even higher selectivity (ca. 1051).

Figure 58:
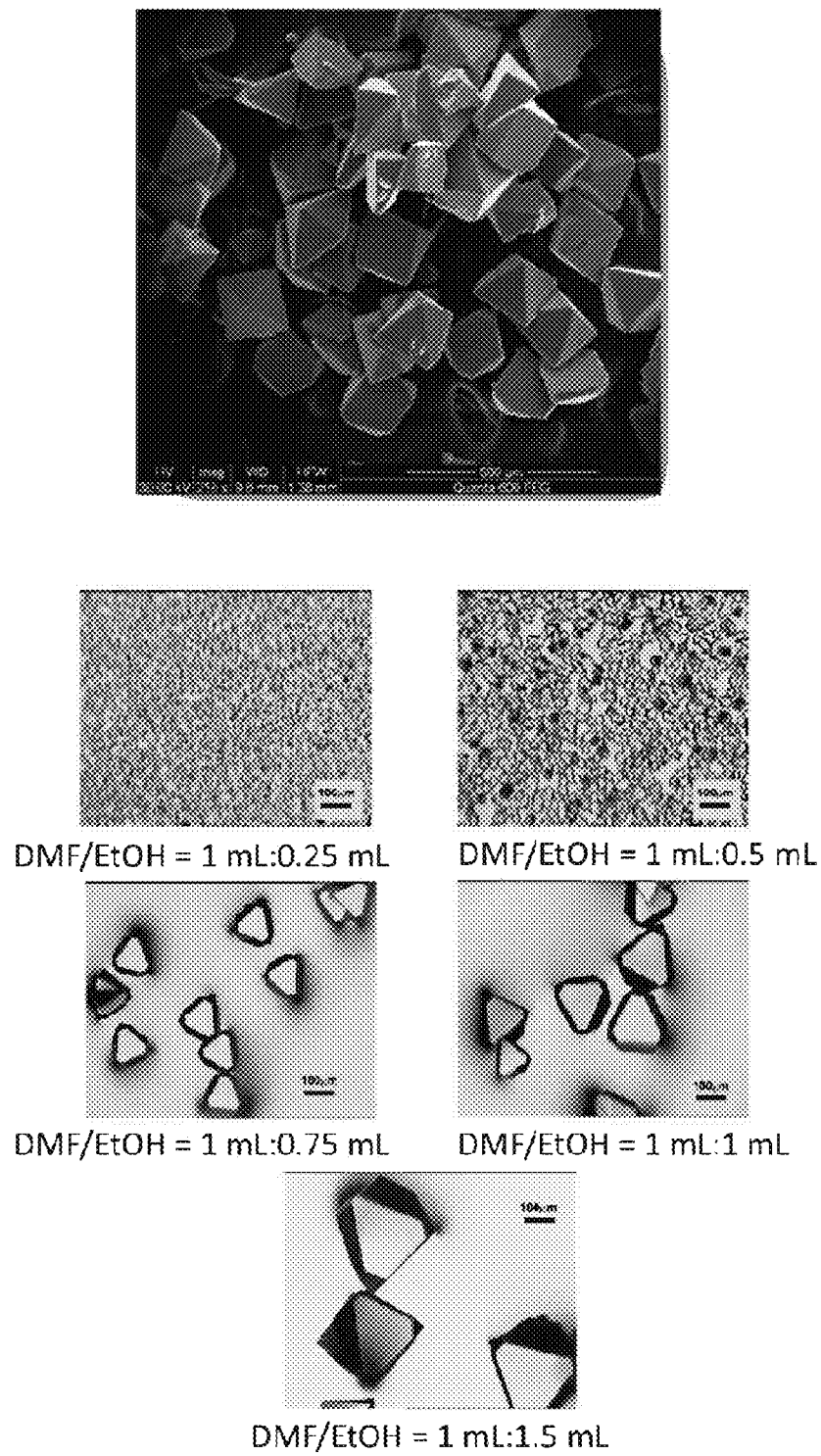
FIG. 58 is a collection of images representing SEM image for compound 1 (top), showing the uniform polyhedral morphology of the crystals and the optical images for compound 3 with different sizes due to varying the ethanol concentration during synthesis (bottom).

The $H_2$ and $CO_2$, as well as other gas, sorption properties were further investigated at high pressure. It was found that at 77 K and 40 bar 1 and 2 store 3.9 and 4.4 wt % of $H_2$, respectively, while for $CO_2$ 7.1 mmol g$^{-1}$ (31.2%) and 9.3 mmol g$^{-1}$ (41.1%) were adsorbed, respectively, at 298 K and 25 bar (FIGS. 51A-51F and 52A-52F). Though these values are lower than those recorded for Mg-MOF-74, they are among the highest $CO_2$ uptakes per surface unit reported at 25 bar. Markedly, when sites I are fully saturated at lower $CO_2$ pressures, the less energetic sites (II and III) dominate the $CO_2$ adsorption at moderately higher $CO_2$ concentration and pressure as reflected by the relatively reduced $CO_2/N_2$ selectivity to ca. 16 at 10% vs. 370 at 0.01%, as determined by IAST (FIG. 58). The predominance of site I, the $CO_2$ sorption high energetic site, can permit efficient $CO_2$ separation at intermediate (10%, flue gas) and high (30-50%, biogas) $CO_2$ concentration.

Figure 10:
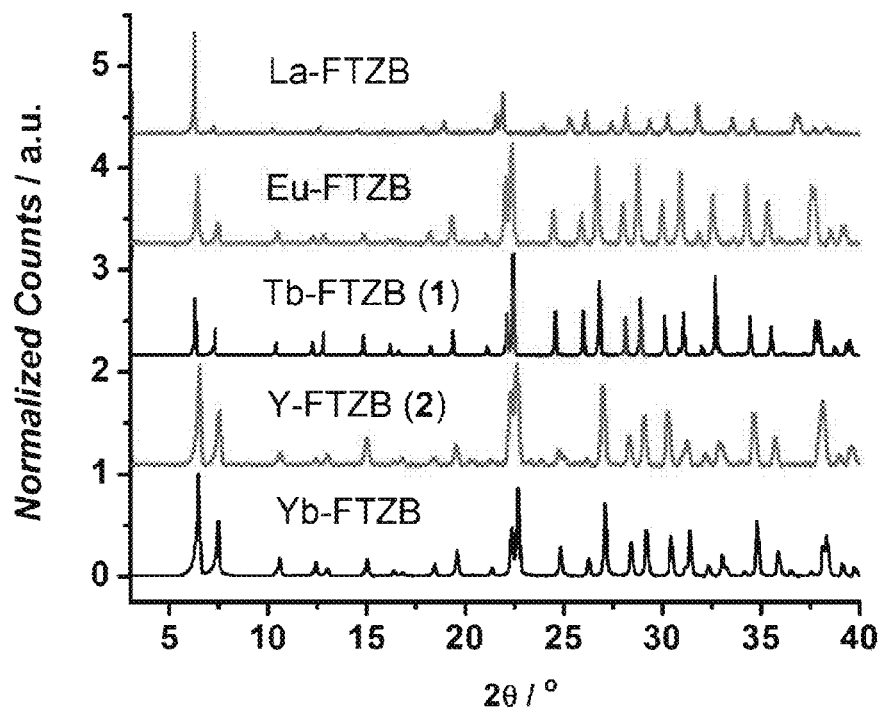
FIG. 10 is a graph representing PXRD patterns of the as-synthesized compounds 1 and 2 compared with the La, Eu and Yb fcu-MOF analogs.

The successful isolation of reaction conditions that consistently permit the in situ generation of the [RE$_6$($\mu_3$-OH)$_8$(O$_2$C—)$_6$(N$_4$C—)$_6$] MBB, and corresponding fcu-MOF platform, offer potential to assess the distinctive role of the fluoro substituent and terazolate moiety on the adsorbate-MOF interactions. Accordingly, various analogous/isoreticular fcu-MOFs were targeted and synthesized, including other RE metal ions (e.g., La$^{3+}$, Eu$^{3+}$ and Yb$^{3+}$) (FIG. 10) and diverse mono-/poly-fluorinated, hetero-/homo-functional, and extended ligands.

Figure 48:
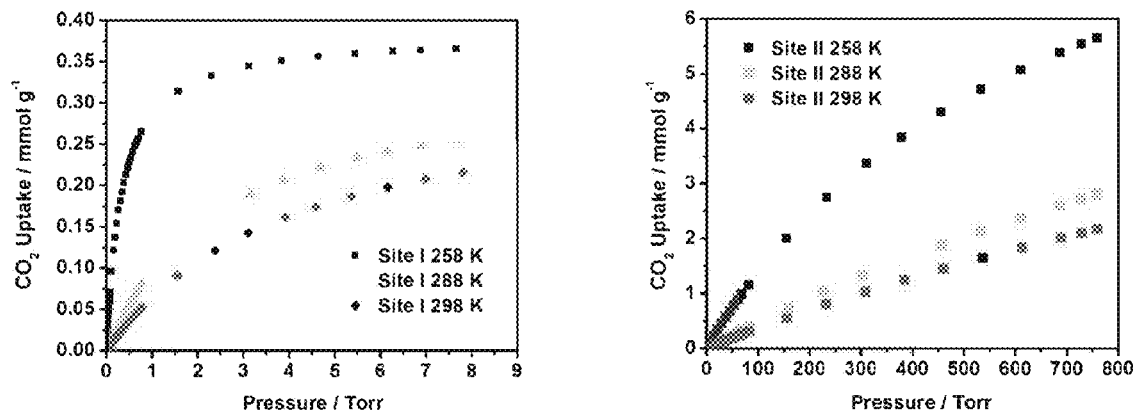
FIG. 48 are graphs representing $CO_2$ adsorption isotherms of compound 3 for sites I and II using the DSL model.
Figure 49:
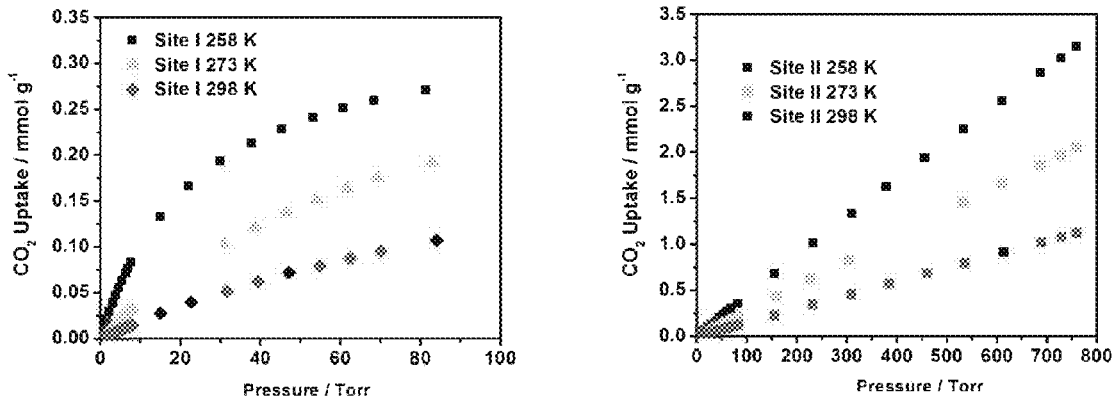
FIG. 49 are graphs representing $CO_2$ adsorption isotherms of compound 6 for sites I and II using the DSL model.

In the first example, the organic linker was expanded from $H_2$FTZB to 3-fluoro-4'-(2H-tetrazol-5-yl)biphenyl-4-carboxylic acid ($H_2$FTZBP) (Scheme 1) and reacted with Tb or Y nitrate salts to give the expected isoreticular compounds, [(CH$_3$)$_2$NH$_2$]$_2$[Tb$_6$($\mu_3$-OH)$_8$(FTZBP)$_6$(H$_2$O)$_6$].x(solvent) (4) or [(CH$_3$)$_2$NH$_2$]$_2$[Y$_6$($\mu_3$-OH)$_8$(FTZBP)$_6$(H$_2$O)$_6$].x(solvent) (5), respectively. As expected, the analogous fluorinated dicarboxylate linker, 3-fluorobiphenyl-4,4'-dicarboxylate (FBPDC, Scheme 1), which is generated in situ via hydrolysis of 4'-cyano-3-fluorobiphenyl-4-carboxylic acid, and 3,3'-difluorobiphenyl-4,4'-dicarboxylic acid ($H_2$DFBPDC, Scheme 1) react with Tb to give the isoreticular analog of 1, denoted as [(CH$_3$)$_2$NH$_2$]$_2$[Tb$_6$($\mu_3$-OH)$_8$(FBPDC)$_6$(H$_2$O)$_6$].x(solvent) (6) and [(CH$_3$)$_2$NH$_2$]$_2$[Tb$_6$($\mu_3$-OH)$_8$(DFBPDC)$_6$(H$_2$O)$_6$].x (solvent) (7), respectively. The $CO_2$ sorption properties were assessed for compounds 3-7, and, as expected, fcu-MOFs constructed from the elongated fluorinated hetero-functional ligand (i.e., 4 and 5) revealed a lower adsorption capacity and reduced $Q_{st}$ values (36.7 and 27.2 kJ mol$^{-1}$, respectively) compared to the parent fcu-MOF based on the shorter and conjugated FTZB ligand. This study clearly supports that reducing the electronic density (by increasing the distance between the fluoro and tetrazolate substituents; i.e., by not having both of them on the same phenyl ring) affords a weaker $CO_2$-framework affinity, which is also directly reflected by the reduced $CO_2$ uptake. Likewise, 3, 6, and 7, from TZB$^{2-}$, FBPDC$^{2-}$ and DFBPDC$^{2-}$ ligands, respectively, have less localized electronic charge density when compared to 1 based on the more polarized FTZB$^{2-}$ ligand, and thus show reduced $CO_2$ adsorption uptakes and relatively lower $Q_{st}$ values for $CO_2$ adsorption at low loading (39.1-46.6 vs 58.1 kJ mol$^{-1}$ for 1). Additionally, MSL analysis performed on the $CO_2$ sorption data for 3 and 6 showed that the best fit and convergence was attained only when the dual site Langmuir was applied (FIG. 48), suggesting the presence of merely two energetic adsorption sites instead of the three energetic sites originally observed in the parent tetrazolate-based fcu-MOFs (e.g., 1 and 2).

Given the unique structural features of this RE-based fcu-MOF platform, the following synergistic combination of effects is likely responsible for the notable $CO_2$ capacity and high affinity towards $CO_2$. These include (i) a high concentration of localized electron-rich vacant metal sites; (ii) the presence of polar groups (i.e., —F, —OH) and nitrogen-rich tetrazolate rings in a confined narrow space and at a proximal vicinity of the open metal sites, favoring multiwall (multisites) interactions with a single $CO_2$ molecule, allowing their interaction with $CO_2$ in a synergistic fashion.

Reaction conditions that consistently permit the in situ generation of the RE$_6$($\mu_3$-OH)$_8$(O$_2$C—)$_6$(N$_4$C—)$_6$] and [RE$_6$($\mu_3$-OH)$_8$(O$_2$C—)$_{12}$] hexanuclear MBBs were isolated and successfully employed for the construction of a series of robust and water stable 12-connected RE-based fcu-MOFs based on fluorinated/non-fluorinated and hetero-/homo-functional ligands. Trivalent RE metal clusters can be assembled into highly-connected MOFs, in this case fcu-MOFs, displaying diverse adsorption energetics toward $CO_2$. The utilization of polarized ligands containing tetrazolate and fluoro moieties afforded enhanced sorption energetic and uptakes due to their unique special positioning, in a narrow proximal vicinity of the open metal sites, offered by the unique fcu-MOF structure. The high $CO_2$ affinity vs. $N_2$, particularly at low pressure, as well as the favorable tolerance to water and high thermal stability, certainly renders 1 and 2 promising prospective adsorbents for low $CO_2$ concentration purification involving multicomponent gas adsorption. Studies are underway to further employ the newly isolated 12-connected [[RE$_6$($\mu_3$-OH)$_8$(O$_2$C—)$_6$(N$_4$C—)$_6$] and [RE$_6$($\mu_3$-OH)$_8$(O$_2$C—)$_{12}$] MBBs for the construction of highly connected MOFs based on hetero-/homo-trifunctional and tetrafunctional ligands with the main objective to increase the concentration per unit surface of the highly energetic sites for $CO_2$ sorption in a wide range of pressures.

Examples

Materials and Methods. The organic ligands used in this study, i.e., 2-fluoro-4-(1H-tetrazol-5-yl)benzoic acid ($H_2$FTZB) and 4-(2Htetrazol-5-yl)benzoic acid ($H_2$TZB), were synthesized from 4-cyano-2-fluorobenzoic acid and 4-cyanobenzoic acid, respectively, with 67 and 74% yields using the Demko-Sharpless method.[14] The organic ligand 3-fluoro-4'-(2H-tetrazol-5-yl)biphenyl-4-carboxylic acid ($H_2FTZBP$) was synthesized from 4'-cyano-3-fluorobiphenyl-4-carboxylic acid according to literature methods.[15] The organic ligand 3,3'-difluorobiphenyl-4,4'-dicarboxylic acid ($H_2DFBPDC$) was synthesized from the following Suzuki homocoupling reaction: A mixture of 4-borono-2-fluorobenzoic acid (2.0 g, 10 mmol), potassium carbonate (1.5 g) and 5% unreduced palladium on carbon (2.0 g) in ethanol (20 mL) was heated at 85° C. for 24 h under nitrogen. The mixture was filtered through a Celite pad, and the solvent was evaporated. Five milliliters of 1.0 M sodium hydroxide were added to dissolve the solid. The solution was acidified by 1.0 M HCl after filtering and extracted in ethyl acetate, dried over $Na_2SO_4$, and filtered, and the volatiles were removed under reduced pressure to yield $H_2DFBPDC$ as a white crystalline solid (0.5 g, 36% yield). $^1H$ NMR (500 MHz, DMF-d7): δ=7.97 (t, J=7.6 Hz, 2 H), 7.69 (q, J=6.4 Hz, 2 H), 7.31-7.39 (m, 2 H). All other reagents were obtained from commercial sources and used without further purification.

Fourier-transform infrared (FT-IR) spectra (4000-600 $cm^{-1}$) were collected in the solid state on a Nicolet 700 FT-IR spectrometer. The peak intensities are described in each of the spectra as very strong (vs), strong (s), medium (m), weak (w), broad (br) and shoulder (sh).

Powder X-ray diffraction (PXRD) measurements were performed on a PANalytical X' Pert PRO MPD X-ray diffractometer at 45 kV, 40 mA for Cu Kα (λ=1.5418 Å) equipped with a variable-temperature stage, with a scan speed of 2°/min. The sample was held at the designated temperatures for at least 10 min between each scan. High resolution dynamic thermogravimetric analysis (TGA) were performed under a continuous $N_2$ flow and recorded on a TA Instruments hi-res TGA Q500 thermogravimetric analyzer with a heating rate of 5° C. per minute. Low pressure gas sorption measurements were performed on a fully automated Autosorb-1C gas sorption analyzer (Quantachrome Instruments). High pressure gas sorption studies were performed on a magnetic suspension balance marketed by Rubotherm (Germany). The SEM image was recorded on a Quanta 600 FEG scanning electron microscope at 30 kV, and the optical images were taken on a CMM-55 microscope. Water vapor sorption measurements were conducted at room temperature on a VTI-SA symmetrical vapor sorption analyzer. Synthesis of Compounds. Synthesis of Tb-FTZB-MOF (1).

$H_2FTZB$ (13.6 mg, 0.0653 mmol), $Tb(NO_3)_3.5H_2O$ (18.9 mg, 0.0435 mmol), DMF (1.0 mL), $C_2H_5OH$ (0.5 mL), and chlorobenzene (0.5 mL) were combined in a 20 mL scintillation vial, sealed and heated to 115° C. for 72 h and cooled to room temperature. The colorless polyhedral crystals were collected and air dried. FT-IR (4000-600 $cm^{-1}$): 3379 (br), 1651 (s), 1611 (m), 1388 (vs), 1251 (w), 1097 (s), 905 (m), 797 (m), 746 (m), 656 (m).

Synthesis of Y-FTZB-MOF (2). $H_2FTZB$ (13.6 mg, 0.0653 mmol), $Y(NO_3)_3.6H_2O$ (16.7 mg, 0.0435 mmol), DMF (1.0 mL), $C_2H_5OH$ (0.5 mL), and chlorobenzene (0.5 mL) were combined in a 20 mL scintillation vial, sealed and were heated to 115° C. for 72 h. The colorless polyhedral crystals were collected and air-dried. FT-IR (4000-600 $cm^{-1}$): 3385 (br), 1658 (s), 1612 (m), 1391 (vs), 1204 (w), 1090 (s), 904 (s), 800 (m), 750 (m), 656 (m).

Synthesis of Tb-TZB-MOF (3). $H_2TZB$ (16.5 mg, 0.087 mmol), $Tb(NO_3)_3.5H_2O$ (18.9 mg, 0.0435 mmol), 2-fluorobenzoic acid (48.7 mg, 0.348 mmol), DMF (1.0 mL), $C_2H_5OH$ (1.5 mL) were combined in a 10 mL microwave tube, sealed and heated to 115° C. for 72 h and cooled to room temperature. The colorless polyhedral crystals were collected and air-dried. FT-IR (4000-600 $cm^{-1}$): 3358 (br), 1656 (s), 1603 (vs), 1659 (s), 1497 (w), 1397 (vs), 1281 (w), 1255 (w), 1176 (w), 1099 (s), 1058 (w), 1011 (m), 878 (w), 840 (w), 801 (m), 751 (s), 701 (w), 663 (w).

Synthesis of Tb-FTZBP-MOF (4). $H_2FTZBP$ (24.7 mg, 0.087 mmol), $Tb(NO_3)_3.5H_2O$ (18.9 mg, 0.0435 mmol), DMF (1.0 mL), $C_2H_5OH$ (0.5 mL), and chlorobenzene (0.5 mL) were combined in a 20 mL scintillation vial, sealed and heated to 115° C. for 72 h and cooled to room temperature. The brown polyhedral crystals were collected and air-dried. FT-IR (4000-600 $cm^{-1}$): 3358 (br), 1650 (vs), 1610 (m), 1411 (m), 1385 (m), 1254 (w), 1099 (s), 1009 (w), 905 (w), 843 (w), 796 (m), 765 (m), 660 (w).

Synthesis of Y-FTZBP-MOF (5). $H_2FTZBP$ (24.7 mg, 0.087 mmol), $Y(NO_3)_3.6H_2O$ (16.8 mg, 0.0435 mmol), DMF (1.0 mL), $C_2H_5OH$ (0.5 mL), and chlorobenzene (0.5 mL) were combined in a 20 mL scintillation vial, sealed and heated to 115° C. for 72 h and cooled to room temperature. The brown polyhedral crystals were collected and air-dried. FT-IR (4000-600 $cm^{-1}$): 3363 (br), 1657 (vs), 1611 (v), 1499 (m), 1412 (m), 1385 (s), 1251 (w), 1097 (s), 1058 (w), 1007 (m), 906 (w), 845 (w), 796 (m), 765 (m), 660 (w).

Synthesis of Tb-FBPDC-MOF (6). 4-Cyano-3-fluorobiphenyl-4-carboxylic acid (41.9 mg, 0.174 mmol), $Tb(NO_3)_3.5H_2O$ (37.8 mg, 0.087 mmol), DMF (1.5 mL), $C_2H_5OH$ (0.5 mL), and chlorobenzene (0.5 mL) were combined in a 20 mL scintillation vial, sealed and heated to 115° C. for 72 h and cooled to room temperature. The colorless polyhedral crystals were collected and air-dried. FT-IR (4000-600 $cm^{-1}$): 3350 (br), 1655 (w), 1584 (vs), 1528 (w), 1382 (vs), 1188 (w), 1109 (m), 1014 (w), 907 (m), 846 (m), 779 (s), 697 (w), 662 (w).

Synthesis of Tb-DFBPDC-MOF (7). $H_2DFBPDC$ (18.2 mg, 0.065 mmol), $Tb(NO_3)_3.5H_2O$ (18.9 mg, 0.0435 mmol), DMF (1.0 mL), $C_2H_5OH$ (0.5 mL), and chlorobenzene (0.5 mL) were combined in a 20 mL scintillation vial, sealed and heated to 115° C. for 60 h and cooled to room temperature. The colorless polyhedral crystals were collected and air-dried. FT-IR (4000-600 $cm^{-1}$): 3338 (br), 1651 (w), 1582 (vs), 1493 (w), 1528 (w), 1385 (vs), 1253 (w), 1209 (w), 1102 (m), 1061 (w), 954 (w), 861 (m), 843 (m), 784 (m), 695 (m).

Low-Pressure Gas Adsorption Measurements

Low pressure gas adsorption studies were conducted on a fully automated micropore gas analyzer Autosorb-1C (Quantachrome Instruments) at relative pressures up to 1 atm. The cryogenic temperature was controlled using liquid nitrogen and argon baths at 77 K and 87 K, respectively. The bath temperature for the $CO_2$ sorption measurements was controlled using a recirculating bath containing an ethylene glycol/$H_2O$ mixture. The apparent surface areas were determined from the argon adsorption isotherms collected at 87 K by applying the Brunauer-Emmett-Teller (BET) and Langmuir models. Pore size analyses were performed using a cylindrical/spherical NLDFT pore model system by assuming an oxidic (zeolitic) surface. The determination of the isosteric heats of adsorption ($Q_{st}$) for $H_2$ and $CO_2$ was estimated by applying the Clausius-Clapeyron expression using the $H_2$ sorption isotherms measured at 77 K and 87 K and the $CO_2$ isotherms measured at 258, 273 and 298 K unless otherwise noted.

Homogenous microcrystalline samples of compounds 1-7 were activated by washing the as-synthesized crystals with 3×20 mL of DMF followed by solvent exchange in methanol (Compounds 1-3) or ethanol (compounds 4-7) for 3 days. The solution was refreshed several times daily during this time period. In a typical experiment, 30 to 40 mg of each activated sample was transferred (dry) to a 6-mm large bulb glass sample cell and firstly evacuated at room temperature using a turbo molecular vacuum pump and then gradually heated to 160° C. for 1, 2, 3 and 7, 120° C. for 4-5 (increasing at a rate of 1° C./min), held for 16 h and cooled to room temperature. Data are presented in Table 2.

TABLE 2

Low pressure sorption data summary for compounds 1-7.

| Compound | BET ($m^2 g^{-1}$) | Langmuir ($m^2 g^{-1}$) | P.V. ($cm^3 g^{-1}$) | $H_2$ Uptake[a] (wt %) | $Q_{st}$ for $H_2$ (kJ $mol^{-1}$) | $CO_2$ Uptake[b] (mmol $g^{-1}$) | $Q_{st}$ for $CO_2$ (kJ $mol^{-1}$) |
|---|---|---|---|---|---|---|---|
| 1 | 1220 | 1510 | 0.51 | 1.96 | 8.69-5.39 | 7.53, 5.86 and 3.54 | 58.1-25.0 |
| 2 | 1310 | 1640 | 0.56 | 2.19 | 9.18-5.68 | 8.33, 6.46 and 4.12 | 46.1-24.0 |
| 3 | 904 | 1145 | 0.39 | 1.47 | 8.45-5.57 | 5.96, 4.53 and 2.50 | 46.6-23.8 |
| 4 | 2200 | 2560 | 0.86 | 1.34 | 8.65-5.06 | 3.93, 2.75 and 1.64 | 36.7-20.3 |
| 5 | 2410 | 2820 | 0.94 | 1.52 | 8.52-4.91 | 4.01, 2.81 and 1.59 | 27.2-19.5 |
| 6 | 1940 | 2330 | 0.78 | 1.37 | 6.84-5.06 | 3.50, 2.40 and 1.37 | 39.1-18.5 |
| 7 | 1854 | 2161 | 0.72 | 1.36 | 7.05-4.99 | 3.91, 2.63 and 1.36 | 41.6-20.7 |

[a] uptake at 77 K and 760 torr;
[b] = $CO_2$ uptake measured at 258, 273 and 298 K respectively.

$CO_2$ Adsorption $Q_{st}$ Analysis on Compounds 1 and 2 Using Multiple-site Langmuir model (MSL)

Equation for MSL: $n = n_{sat1}*b_1 p/1+b_1 p + n_{sat2}*b_2 p/1+b_2 p + \ldots + n_{sati}*b_i p/1+b_i p$ The best fit and convergence were obtained with the triple site Langmuir (TSL) model. The parameters extracted from the best TSL fit were used to recalculate the adsorption isotherms and the evolution of the $Q_{st}$ for each energetic site (site I, site II and site III) using the Clausius-Clapeyron equation.

TABLE S2

Triple site Langmuir parameters (Compound 1)

| Parameters | | Temperature/K | |
| | | 258 | 273 | 298 |
|---|---|---|---|---|
| Adsorption Site I | $n_{sat1}$ | 0.33956 | 0.27756 | 0.26915 |
| | $b_1$ | 147.49445 | 48.15585 | 5.50219 |
| Adsorption Site II | $n_{sat2}$ | 0.37026 | 0.40104 | 0.42827 |
| | $b_2$ | 4.91024 | 1.58224 | 0.22432 |
| Adsorption Site III | $n_{sat3}$ | 10.86539 | 11.18523 | 15.24316 |
| | $b_3$ | 0.01703 | 0.00865 | 0.00231 |

TABLE S3

Triple site Langmuir parameters (Compound 2)

| Parameters | | Temperature/K | |
| | | 258 | 273 | 298 |
|---|---|---|---|---|
| Adsorption Site I | $n_{sat1}$ | 0.39195 | 0.35252 | 0.29521 |
| | $b_1$ | 259.98806 | 80.03201 | 23.96898 |
| Adsorption Site II | $n_{sat2}$ | 0.52812 | 0.5334 | 0.62601 |
| | $b_2$ | 9.75852 | 2.64722 | 0.83725 |
| Adsorption Site III | $n_{sat3}$ | 11.82402 | 12.0789 | 12.99557 |
| | $b_3$ | 0.01696 | 0.00859 | 0.00326 |

High-Pressure Gas Adsorption Measurements

Figure 50:
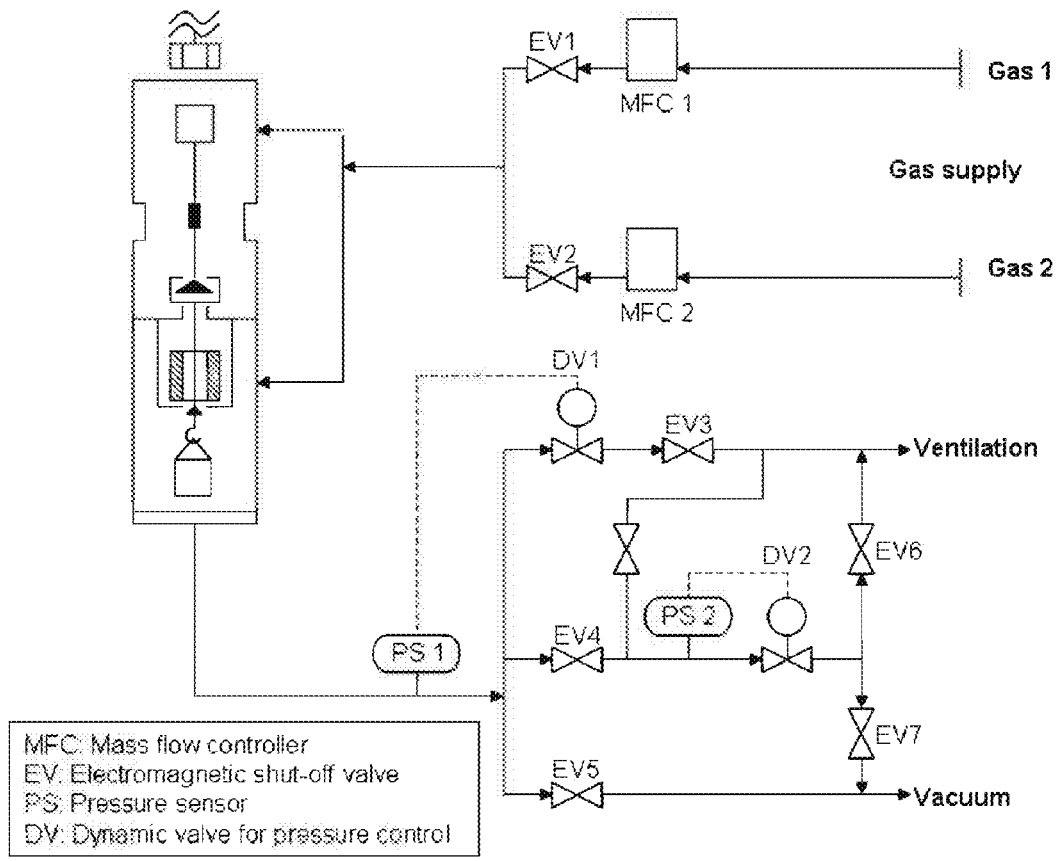
FIG. 50 is a schematic diagram representing the Rubotherm gravimetric-densimetric apparatus.
Figure 51A:
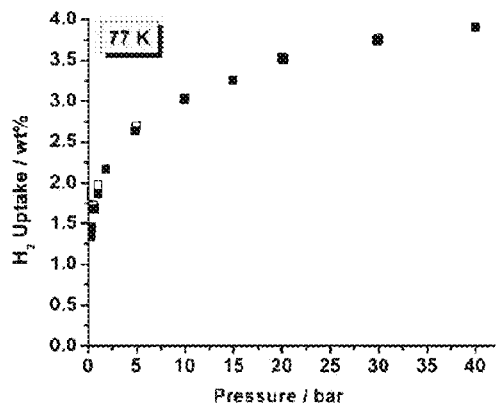
FIGS. 51A-51F are graphs representing excess high-pressure sorption isotherms for compound 1: $H_2$, $CO_2$, $CH_4$, $N_2$ and $O_2$. The adsorption and desorption branches are represented as solid and open symbols, respectively.
Figure 51B:
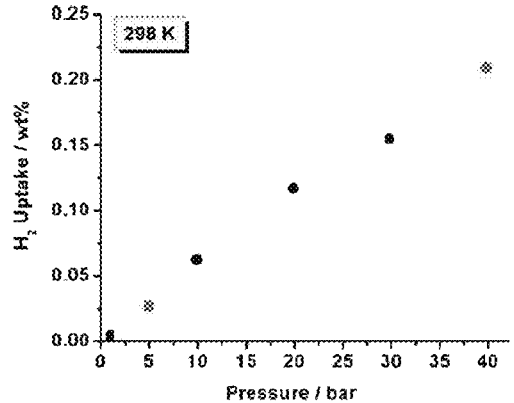
Figure 51C:
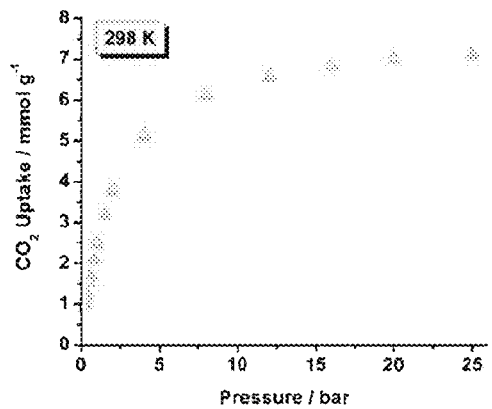
Figure 51D:
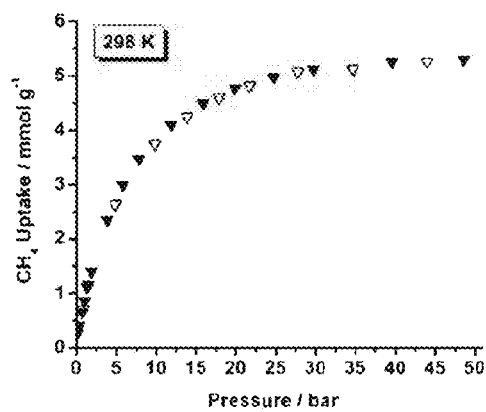
Figure 51E:
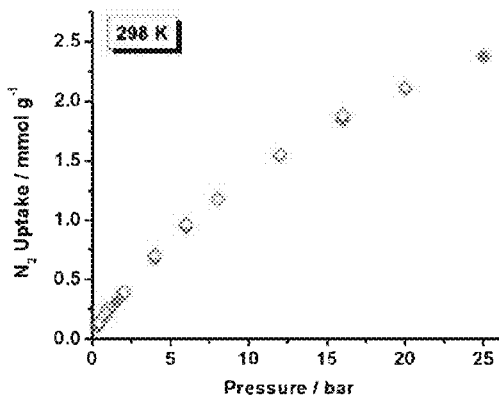
Figure 51F:
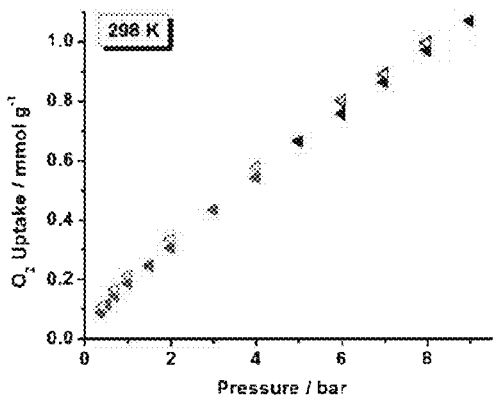
Figure 52A:
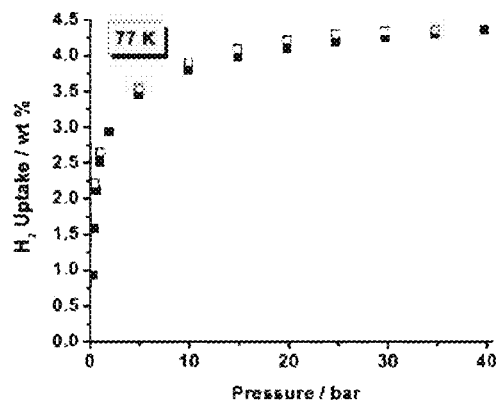
FIG. 52A-52F are graphs representing excess high-pressure sorption isotherms for compound 2: $H_2$, $CO_2$, $CH_4$, $N_2$ and $O_2$. The adsorption and desorption branches are represented as solid and open symbols, respectively.
Figure 52B:
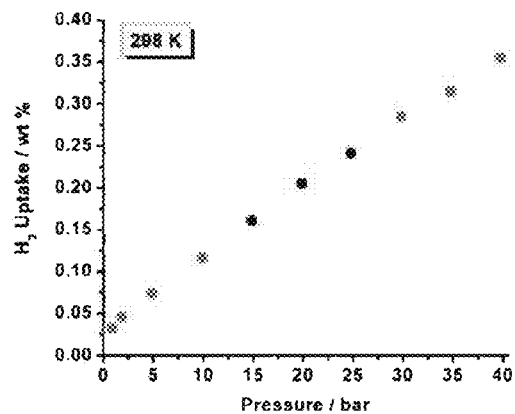
Figure 52C:
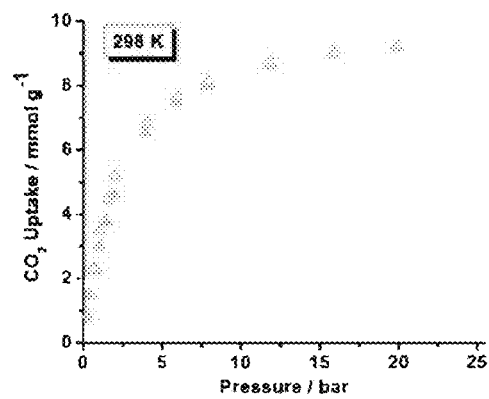
Figure 52D:
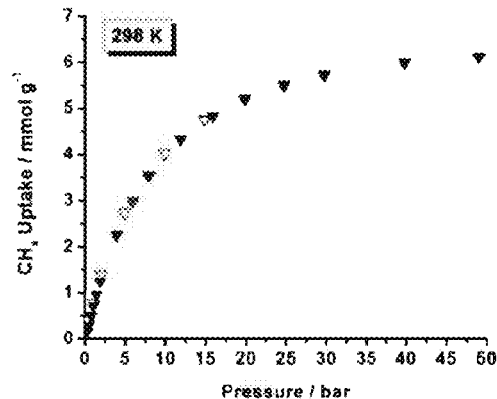
Figure 52E:
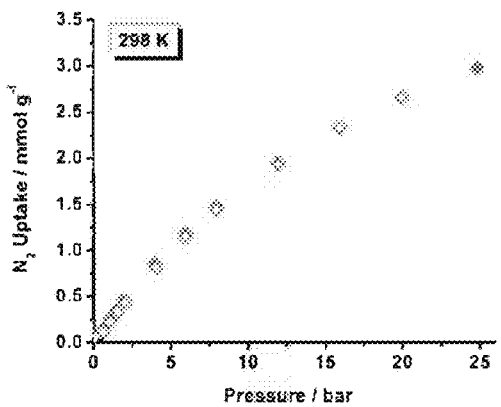
Figure 52F:
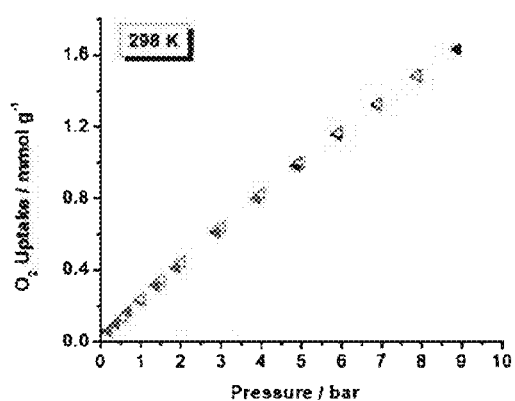
Figure 53A:
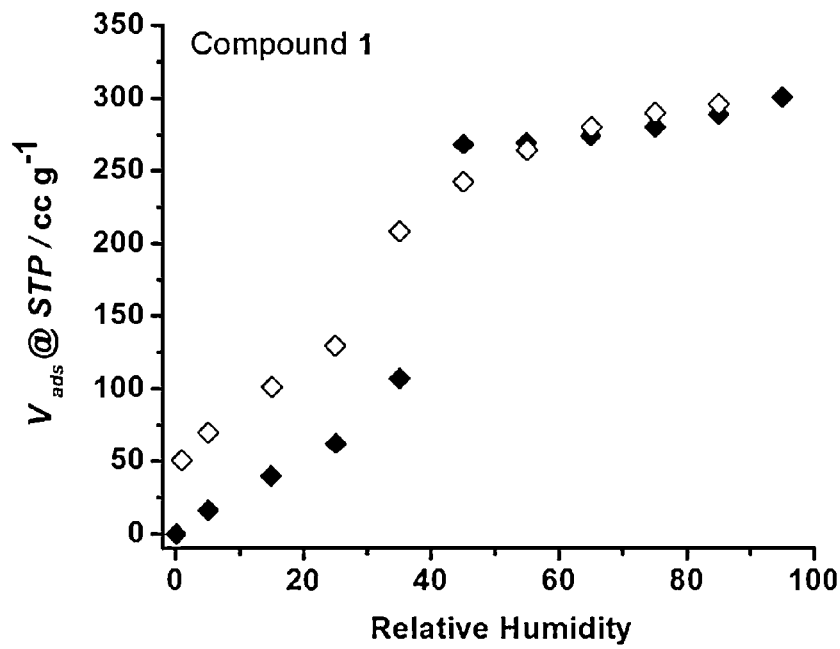
FIGS. 53A and 53B are graphs representing water vapor sorption isotherms collected at 298 K for compound 1 (top) and compound 2 (bottom) with adsorption (solid symbols) and desorption (open symbols) points, showing that both materials are tolerant to water. Note that the last desorption point corresponds to the coordinated water molecules in each material, i.e., 5.50 water per Tb6 cluster and 5.76 water per Y6 cluster.
Figure 53B:
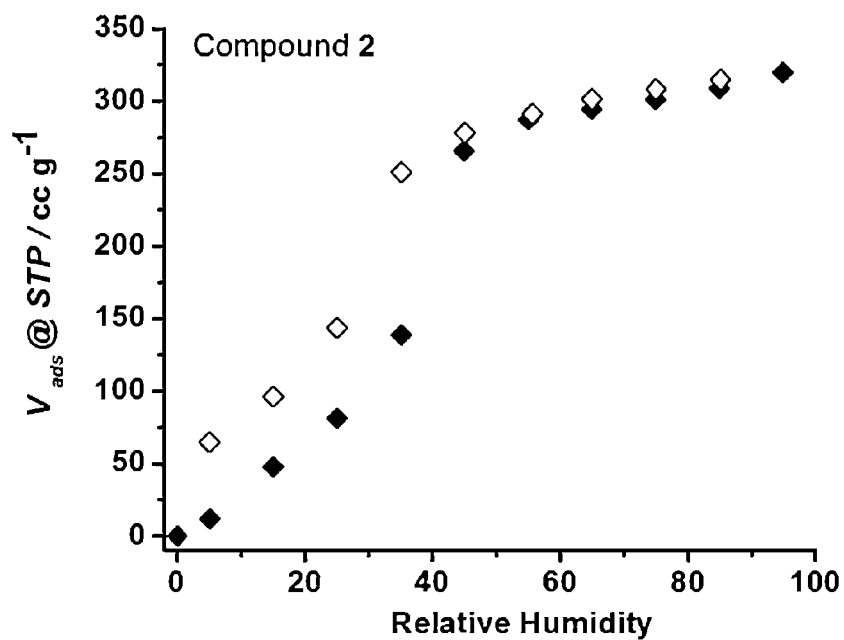

Adsorption equilibrium measurements for the pure gases were performed using a Rubotherm gravimetric-densimetric apparatus (Bochum, Germany) (FIG. 50), composed mainly of a magnetic suspension balance (MSB) and a network of valves, mass flowmeters and temperature and pressure sensors. The MSB overcomes the disadvantages of other commercially available gravimetric instruments by separating the sensitive microbalance from the sample and the measuring atmosphere and is able to perform adsorption measurements across a wide pressure range, i.e. 0 to 200 bar. Moreover, the adsorption temperature can be controlled in the range of 77 K to 423 K. In a typical adsorption experiment, the adsorbent is precisely weighed and placed in a basket suspended by a permanent magnet through an electromagnet. The cell in which the basket is housed is then closed and vacuum or high pressure is applied. The gravimetric method allows the direct measurement of the reduced gas adsorbed amount $\Omega$. Correction for the buoyancy effect is required to determine the excess adsorbed amount using equation 1, where $V_{adsorbent}$ and $V_{ss}$ refer to the volume of the adsorbent and the volume of the suspension system, respectively. These volumes are determined using the helium isotherm method by assuming that helium penetrates in all open pores of the materials without being adsorbed. The density of the gas is determined using Refprop equation of state (EOS) database and checked experimentally using a volume-calibrated titanium cylinder. By weighing this calibrated volume in the gas atmosphere, the local density of the gas is also determined. Simultaneous measurement of adsorption capacity and gas phase density as a function of pressure and temperature is therefore possible. The excess uptake is the only experimentally accessible quantity and there is no reliable experimental method to determine the absolute uptake. For this reason, only the excess amounts are considered in this work.

$$\Omega = m_{excess} - \rho_{gas}(V_{adsorbent} + V_{ss}) \qquad (1)$$

The pressure is measured using two Drucks high pressure transmitters ranging from 0.5 to 34 bar and 1 to 200 bar, respectively, and one low pressure transmitter ranging from 0 to 1 bar. Prior to each adsorption experiment, about 100 mg to 300 mg sample is outgassed at 433 K at a residual pressure $10^{-4}$ mbar. The temperature during adsorption measurements is held constant by using a thermostated circulating fluid.

Figure 55:
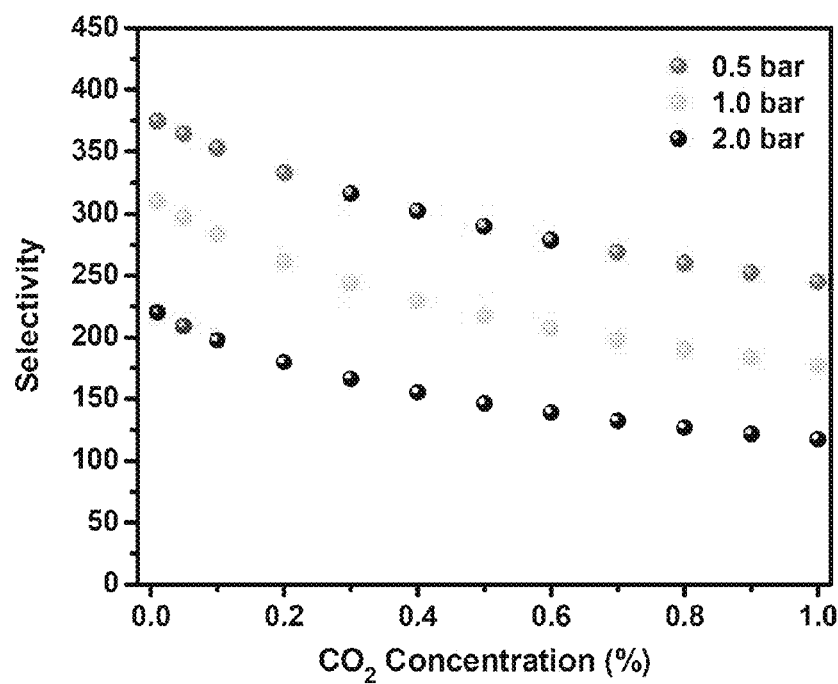
FIG. 55 are graphs representing $CO_2$ selectivity over $N_2$ resulted from the interaction with site I at 298 K at different total pressures in 0.5-2 barrange calculated using IAST for compound 1.

FIG. 55 shows the selectivity of $CO_2$ over $N_2$ at 298 K, calculated (using IAST)[c] from levels of a few ppm to 1%, assuming $CO_2$ interaction with compound 1 are completely governed by adsorption on site I. The selectivity was calculated assuming different total pressures for the mixtures (i.e., 0.5, 1 and 2 bar). The purpose of the total pressure variation is to mimic vacuum swing adsorption (VSA) regeneration mode conditions supposing 0.2, 0.5 and 1 bar as the working adsorption pressure and vacuum as the desorption pressure. As was expected, the $CO_2$ selectivity over $N_2$ was high (ca. 370) in the domain when interaction with site I are the most dominant. Prediction of $CO_2/N_2$ selectivity at variable total pressures from 0.5 bar and up to 2 bar showed that the $CO_2/N_2$ separation decreased by increasing the total pressure and concentration due to the quick saturation of most of energetics sites (site I) available. Therefore a way to maintain high selectivity is to increase the density of site I. In order to confirm this finding, breakthrough adsorption experiments were carried out using a $CO_2/N_2$ mixture containing 1000 ppm of $CO_2$ at 298 K and a total pressure of 1 bar. The purpose of using such low concentration is to explore experimentally the separation performance of the compound 1 where the adsorption is mostly governed by the most energetic site (site I).

Figure 56:
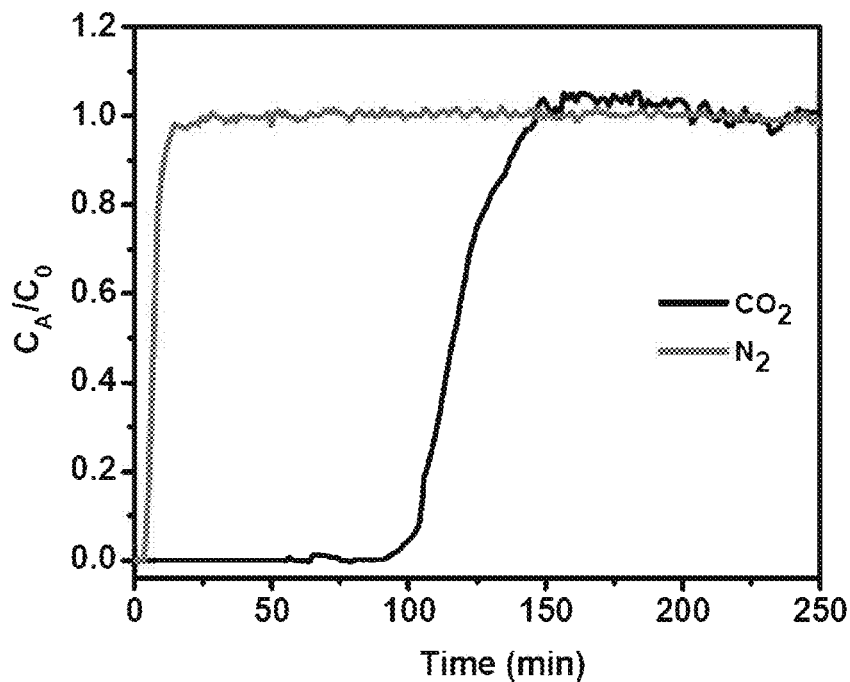
FIG. 56 is a graph representing experimental breakthrough test of traces (1000 ppm) $CO_2$ in mixture with $N_2$ on compound 1.

Interestingly, the breakthrough test shows that the $CO_2$ was retained in the bed for ca. 5250 s while $N_2$ breakthrough occurred almost after few second (FIG. 56). The gas uptake for $CO_2$ and $N_2$ at breakthrough was 0.262 and 0.249 mmol/g. Therefore, the $CO_2/N_2$ selectivity was exceptionally high (ca. 1051) exceeding the predicted selectivity using IAST. This finding is extremely important as it shows that materials with high density of adsorption site I will certainly lead to suitable separation agents for $CO_2$ removal from gas streams with even higher $CO_2$ concentration (10-30%) in order to produce useful commodities such as $CH_4$, $O_2$ and $H_2$ with higher efficiency. Ongoing work is focusing on the design of new MOFs with such attributes.

Single Crystal X-ray Crystallography. Single-crystal X-ray diffraction data were collected using a Bruker-AXS SMART-APEX2 CCD diffractometer (Cu Kα, λ=1.54178 Å) for compounds 1 and 2, Bruker X8 PROSPECTOR APEX2 CCD (Cu Kα, λ=1.54178 Å) for compounds 3 and 5-7, and Oxford Supernova Atlas CCD (Mo Kα=0.71073 Å) for compound 4. Indexing was performed using APEX2 (Difference Vectors method).16 Data integration and reduction were performed using SaintPlus 6.01. Bruker SAINT, Data Reduction Software; Bruker AXS, Inc.: Madison, Wis., 2009, which is incorporated by reference in its entirety. Absorption correction was performed by multiscan method implemented in SADABS. Sheldrick, G. M. SADABS, Program for Empirical Absorption Correction; University of Gottingen: Gottingen, Germany, 2008, which is incorporated by reference in its entirety. Space groups were determined using XPREP implemented in APEX2. Bruker APEX2; Bruker AXS, Inc.: Madison, Wis., 2010, which is incorporated by reference in its entirety. Structures were solved using SHELXS-97 (direct methods) and refined using SHELXL-97 (full-matrix least-squares on F2) contained in APEX216 and WinGX v1.70.01 programs packages. See, for example, (a) Farrugia, L. J. Appl. Crystallogr. 1999, 32, 837-838, and Sheldrick, G. M. SHELXL-97, Program for the Refinement of Crystal; University of Gottingen: Gottingen, Germany, 1997. (c) Sheldrick, G. M. Acta Crystallogr. 1990, A46, 467-473. (d) Sheldrick, G. M. Acta Crystallogr. 2008, A64, 112-122, each of which is incorporated by reference in its entirety. CrysAlis Pro package was used to process diffraction images for compound 4. CrysAlis Pro; Oxford Diffraction: Abingdon, U.K., 2009, which is incorporated by reference in its entirety. For all compounds the ligand moiety was disordered and atoms were refined using geometry restraints. Restraints were also used to refine anisotropic displacement parameters of disordered atoms. Disordered cations and solvent molecules were refined isotropically. Relatively high residual electron density observed in a μ-OH position (leading to very small value of thermal parameters for μ-OH oxygen) are most likely attributed to "electron transfer ( . . . ) directed from d-orbitals to the oxygen 2p orbitals", which is observed in yttrium-oxide clusters. Pramann, A.; Nakamura, Y.; Nakijama, A.; Kaya, K. J. Phys. Chem. A 2001, 105, 7534-7540, which is incorporated by reference in its entirety. Hydrogen atoms were placed in geometrically calculated positions and included in the refinement process using riding model with isotropic thermal parameters: $U_{iso}$(H)=1.2 Ueq(—OH, —CH).

The crystal of compound 7 was twinned, twinning law [−0.66/−0.33/0.66] [0.66/−0.66/0.33] [0.33/0.66/0.66]. Two reciprocal lattices have been identified using XPREP (APEX2); diffraction data have been integrated using SAINT and scaled/corrected using TWINABS. Sheldrick, G. M. TWINABS; Bruker AXS, Inc.; Madison, Wis., 2002, which is incorporated by reference in its entirety. Refinement has been carried using HKLF 5 style reflection data containing reflection from both domains (BASF=0.12). Distance restraints have been used to refine disordered benzene rings.

Disordered atoms have been refined isotropically. For compounds 3-7, the contribution of heavily disordered solvent molecules was treated as diffuse using Squeeze procedure implemented in Platon program. Spek, T. L. Acta Crystallogr. 1990, A46, 194-201, which is incorporated by reference in its entirety. Crystal data and refinement conditions are shown in Tables 3-11.

TABLE 3

Selected Low Pressure Sorption Data for Compounds 1-7

| compound | 1 | 2 | 3 | 4 | 5 | 6 | 7 |
|---|---|---|---|---|---|---|---|
| BET (m² g⁻¹) | 1220 | 1310 | 904 | 2200 | 2410 | 1940 | 1854 |
| PV (cm³ g⁻¹) | 0.51 | 0.56 | 0.39 | 0.86 | 0.94 | 0.78 | 0.72 |
| $CO_2$ uptake[a] (mmol g⁻¹) | 7.53, 5.86, and 3.54 | 8.33, 6.46, and 4.12 | 5.96, 4.53, and 2.50 | 3.93, 2.75, and 1.64 | 4.01, 2.81, and 1.59 | 3.50, 2.40, and 1.37 | 3.91, 2.63, and 1.36 |
| $Q_{st}$ for $CO_2$ (kJ mol⁻¹) | 58.1-25.0 | 46.1-24.0 | 46.6-23.8 | 36.7-20.3 | 27.2-19.5 | 39.1-18.5 | 41.6-20.7 |

[a]$CO_2$ uptake at 760 Torr measured at 258, 273, and 298 K, respectively.

TABLE 4

Selected Crystallographic Data and Structural Refinement for Compounds 1-7

| compound | 1 | 2 | 3 | 4 | 5 | 6 | 7 |
|---|---|---|---|---|---|---|---|
| formula | $C_{52}H_{18}Tb_6N_{26}O_{48}F_6$ | $C_{52}H_{18}Y_6N_{26}O_{78}F_6$ | $C_{48}H_{32}Tb_6N_{24}O_{58}$ | $C_{84}H_{42}Tb_6N_{24}O_{26}F_6$ | $C_{84}H_{42}Y_6N_{24}O_{26}F_6$ | $C_{84}H_{42}Tb_6O_{38}F_6$ | $C_{84}H_{36}Tb_6O_{46}F_{32}$ |
| FW (g mol$^{-1}$) | 2842.44 | 2902.38 | 2826.43 | 2870.94 | 2450.88 | 2726.70 | 2962.65 |
| crystal system | cubic | cubic | cubic | cubic | cubic | cubic | cubic |
| space group | $Fm\bar{3}m$ | $Fm\bar{3}m$ | $Fm\bar{3}m$ | $Fm\bar{3}m$ | $Fm\bar{3}m$ | $Fm\bar{3}m$ | $Fm\bar{3}m$ |
| a (Å) | 23.5553(2) | 23.4365(4) | 23.5195(5) | 29.5957(3) | 29.447(3) | 27.5127(12) | 27.4756(7) |
| V (Å$^3$) | 13069.7(2) | 12873.0(4) | 13010.2(5) | 25923.0(5) | 25535(4) | 20825.7(16) | 20741.6(9) |
| Z, $D_{cal}$ (g cm$^{-3}$) | 4, 1.445 | 4, 1.498 | 4, 1.439 | 4, 0.736 | 4, 0.638 | 4, 0.870 | 4, 0.949 |
| $\theta_{max}$ (°) | 65.74 | 63.48 | 67.93 | 28.27 | 65.64 | 63.44 | 67.93 |
| $R_{int}$ | 0.0610 | 0.0313 | 0.0380 | 0.0289 | 0.0198 | 0.0442 | 0.000 |
| $R_1$ (I > 2σ(I$_0$)) | 0.0359 | 0.0395 | 0.0340 | 0.0236 | 0.0337 | 0.0402 | 0.0732 |
| $wR_2$ (all data) | 0.1315 | 0.1183 | 0.1031 | 0.0724 | 0.1016 | 0.1125 | 0.2085 |
| GOF | 1.099 | 1.052 | 1.086 | 1.072 | 1.059 | 1.051 | 1.051 |
| $\Delta\rho_{max}/\Delta\rho_{min}$ (e · Å$^{-3}$) | 1.559/−0.396 | 1.849/−0.597 | 1.161/−0.493 | 1.128/−0.532 | 0.675/−0.283 | 0.839/−0.716 | 1.137/−1.339 |

TABLE 5

Crystal data and structure refinement for compound Tb-FTZB-MOF (1)

| | |
|---|---|
| Identification code | 1 |
| Empirical formula | $C_{52}H_{18}F_6N_{26}O_{48}Tb_6$ |
| Formula weight | 2842.44 |
| Temperature | 100(2) K |
| Wavelength | 1.54178 Å |
| Crystal system, space group | Cubic, Fm-3m |
| Unit cell dimensions | a = 23.5553(2) Å alpha = 90 deg. |
| | b = 23.5553(2) Å beta = 90 deg. |
| | c = 23.5553(2) Å gamma = 90 deg. |
| Volume | 13069.71(19) Å$^3$ |
| Z, Calculated density | 4, 1.445 Mg/m$^3$ |
| Absorption coefficient | 16.373 mm$^{-1}$ |
| F(000) | 5360 |
| Crystal size | 0.10 × 0.10 × 0.10 mm |
| Theta range for data collection | 5.31 to 65.74 deg. |
| Limiting indices | −19 <= h <= 26, −27 <= k <= 27, −27 <= l <= 24 |
| Reflections collected/unique | 14184/637 [R(int) = 0.0610] |
| Completeness to theta = 65.74 | 99.4% |
| Absorption correction | Semi-empirical from equivalents |
| Max. and min. transmission | 0.2913 and 0.2913 |
| Refinement method | Full-matrix least-squares on F$^2$ |
| Data/restraints/parameters | 626/57/81 |
| Goodness-of-fit on F$^2$ | 1.099 |
| Final R indices [I > 2sigma(I)] | $R_1$ = 0.0359, $wR_2$ = 0.1294 |
| R indices (all data) | $R_1$ = 0.0401, $wR_2$ = 0.1315 |
| Largest diff. peak and hole | 1.559 and −0.396 e. Å$^{-3}$ |

TABLE 6

Crystal data and structure refinement for compound Y-FTZB-MOF (2)

| | |
|---|---|
| Identification code | 2 |
| Empirical formula | $C_{52}H_{18}F_6N_{26}O_{78}Y_6$ |
| Formula weight | 2902.38 |
| Temperature | 100(2) K |
| Wavelength | 1.54178 Å |
| Crystal system, space group | Cubic, Fm-3m |
| Unit cell dimensions | a = 23.4365(4) Å alpha = 90 deg. |
| | b = 23.4365(4) Å beta = 90 deg. |
| | c = 23.4365(4) Å gamma = 90 deg. |
| Volume | 12873.0(4) Å$^3$ |
| Z, Calculated density | 4, 1.498 Mg/m$^3$ |
| Absorption coefficient | 4.527 mm$^{-1}$ |
| F(000) | 5696 |
| Crystal size | 0.10 × 0.10 × 0.10 mm |
| Theta range for data collection | 5.34 to 63.48 deg. |
| Limiting indices | −27 <= h <= 25, −18 <= k <= 27, −17 <= l <= 10 |
| Reflections collected/unique | 5335/575 [R(int) = 0.0313] |
| Completeness to theta = 63.48 | 97.0% |
| Absorption correction | Semi-empirical from equivalents |
| Max. and min. transmission | 0.6603 and 0.6603 |
| Refinement method | Full-matrix least-squares on F$^2$ |
| Data/restraints/parameters | 575/69/88 |
| Goodness-of-fit on F$^2$ | 1.052 |
| Final R indices [I > 2sigma(I)] | $R_1$ = 0.0395, $wR_2$ = 0.1160 |
| R indices (all data) | $R_1$ = 0.0414, $wR_2$ = 0.1183 |
| Largest diff. peak and hole | 1.849 and −0.597 e. Å$^{-3}$ |

TABLE 7

Crystal data and structure refinement for compound Tb-TZB-MOF (3)

| | |
|---|---|
| Identification code | 3 |
| Empirical formula | $C_{48}H_{32}N_{24}O_{58}Tb_6$ |
| Formula weight | 2826.43 |
| Temperature | 100(2) K |
| Wavelength | 1.54178 Å |
| Crystal system, space group | Cubic, Fm-3m |
| Unit cell dimensions | a = 23.5195(5) Å alpha = 90 deg. |
| | b = 23.5195(5) Å beta = 90 deg. |
| | c = 23.5195(5) Å gamma = 90 deg. |
| Volume | 13010.2(5) Å$^3$ |
| Z, Calculated density | 4, 1.439 Mg/m$^3$ |
| Absorption coefficient | 16.428 mm$^{-1}$ |
| F(000) | 5336 |
| Crystal size | 0.10 × 0.10 × 0.10 mm |
| Theta range for data collection | 5.32 to 67.93 deg. |
| Limiting indices | −26 <= h <= 22, −20 <= k <= 18, −22 <= l <= 27 |
| Reflections collected/unique | 10330/624 [R(int) = 0.0380] |
| Completeness to theta = 65.93 | 99.0% |
| Absorption correction | Semi-empirical from equivalents |
| Max. and min. transmission | 0.2904 and 0.2904 |
| Refinement method | Full-matrix least-squares on F$^2$ |
| Data/restraints/parameters | 624/1/64 |
| Goodness-of-fit on F$^2$ | 1.086 |
| Final R indices [I > 2sigma(I)] | $R_1$ = 0.0340, $wR_2$ = 0.1028 |
| R indices (all data) | $R_1$ = 0.0343, $wR_2$ = 0.1031 |
| Largest diff. peak and hole | 1.161 and −0.493 e. Å$^{-3}$ |

TABLE 8

Crystal data and structure refinement for compound Tb-FTZBP-MOF (4)

| | |
|---|---|
| Identification code | 34 |
| Empirical formula | $C_{84}H_{42}F_6N_{24}O_{26}Tb_6$ |
| Formula weight | 2870.94 |
| Temperature | 200(2) K |
| Wavelength | 0.71073 Å |
| Crystal system, space group | Cubic, Fm-3m |
| Unit cell dimensions | a = 29.5957(3) Å alpha = 90 deg. |
| | b = 29.5957(3) Å beta = 90 deg. |
| | c = 29.5957(3) Å gamma = 90 deg. |
| Volume | 25923.0(5) Å$^3$ |
| Z, Calculated density | 4, 0.736 Mg/m$^3$ |
| Absorption coefficient | 1.651 mm$^{-1}$ |
| F(000) | 5464 |
| Crystal size | 0.20 × 0.20 × 0.20 mm |
| Theta range for data collection | 3.58 to 28.27 deg. |
| Limiting indices | −23 <= h <= 29, −30 <= k <= 8, −21 <= l <= 37 |
| Reflections collected/unique | 6198/1586 [R(int) = 0.0289] |
| Completeness to theta = 27.0 | 99.0% |
| Absorption correction | Semi-empirical from equivalents |
| Max. and min. transmission | 0.7336 and 0.7336 |
| Refinement method | Full-matrix least-squares on F$^2$ |
| Data/restraints/parameters | 1586/50/89 |
| Goodness-of-fit on F$^2$ | 1.072 |
| Final R indices [I > 2sigma(I)] | $R_1 = 0.0236$, $wR_2 = 0.0715$ |
| R indices (all data) | $R_1 = 0.0264$, $wR_2 = 0.0724$ |
| Largest diff. peak and hole | 1.128 and −0.532 e. Å$^{-3}$ |

TABLE 9

Crystal data and structure refinement for compound Y-FTZBP-MOF (5)

| | |
|---|---|
| Identification code | 5 |
| Empirical formula | $C_{84}H_{42}F_6N_{24}O_{26}Y_6$ |
| Formula weight | 2450.88 |
| Temperature | 100(2) K |
| Wavelength | 1.54178 Å |
| Crystal system, space group | Cubic, Fm-3m |
| Unit cell dimensions | a = 29.447(3) Å alpha = 90 deg. |
| | b = 29.447(3) Å beta = 90 deg. |
| | c = 29.447(3) Å gamma = 90 deg. |
| Volume | 25535(4) Å$^3$ |
| Z, Calculated density | 4, 0.638 Mg/m$^3$ |
| Absorption coefficient | 2.074 mm$^{-1}$ |
| F(000) | 4840 |
| Crystal size | 0.20 × 0.20 × 0.20 mm |
| Theta range for data collection | 6.01 to 65.64 deg. |
| Limiting indices | −34 <= h <= 24, −34 <= k <= 34, −23 <= l <= 33 |
| Reflections collected/unique | 20849/1148 [R(int) = 0.0198] |
| Completeness to theta = 65.64 | 98.3% |
| Absorption correction | Semi-empirical from equivalents |
| Max. and min. transmission | 0.6818 and 0.6818 |
| Refinement method | Full-matrix least-squares on F$^2$ |
| Data/restraints/parameters | 1148/71/89 |
| Goodness-of-fit on F$^2$ | 1.059 |
| Final R indices [I > 2sigma(I)] | $R_1 = 0.0337$, $wR_2 = 0.1010$ |
| R indices (all data) | $R_1 = 0.0340$, $wR_2 = 0.1016$ |
| Largest diff. peak and hole | 0.675 and −0.283 e. Å$^{-3}$ |

TABLE 10

Crystal data and structure refinement for compound Tb-FBPDC-MOF (6)

| | |
|---|---|
| Identification code | 6 |
| Empirical formula | $C_{84}H_{42}F_6O_{38}Tb_6$ |
| Formula weight | 2726.70 |
| Temperature | 100(2) K |
| Wavelength | 1.54178 Å |
| Crystal system, space group | Cubic, Fm-3m |
| Unit cell dimensions | a = 27.5127(12) Å alpha = 90 deg. |
| | b = 27.5127(12) Å beta = 90 deg. |
| | c = 27.5127(12) Å gamma = 90 deg. |
| Volume | 20825.7(16) Å$^3$ |
| Z, Calculated density | 4, 0.870 Mg/m$^3$ |
| Absorption coefficient | 10.186 mm$^{-1}$ |
| F(000) | 5176 |
| Crystal size | 0.10 × 0.10 × 0.10 mm |
| Theta range for data collection | 2.78 to 63.44 deg. |
| Limiting indices | −26 <= h <= 31, −29 <= k <= 31, −26 <= l <= 31 |
| Reflections collected/unique | 20823/917 [R(int) = 0.0442] |
| Completeness to theta = 63.44 | 99.6% |
| Absorption correction | Semi-empirical from equivalents |
| Max. and min. transmission | 0.4290 and 0.4290 |
| Refinement method | Full-matrix least-squares on F$^2$ |
| Data/restraints/parameters | 917/38/59 |
| Goodness-of-fit on F$^2$ | 1.051 |
| Final R indices [I > 2sigma(I)] | $R_1 = 0.0402$, $wR_2 = 0.1105$ |
| R indices (all data) | $R_1 = 0.0420$, $wR_2 = 0.1125$ |
| Largest diff. peak and hole | 0.839 and −0.716 e. Å$^{-3}$ |

TABLE 11

Crystal data and structure refinement for compound Tb-DFBPDC-MOF (7)

| | |
|---|---|
| Identification code | 7 |
| Empirical formula | $C_{84}H_{36}F_{12}O_{46}Tb_6$ |
| Formula weight | 2962.65 |
| Temperature | 100(2) K |
| Wavelength | 1.54178 Å |
| Crystal system, space group | Cubic, Fm-3m |
| Unit cell dimensions | a = 27.4756(7) Å alpha = 90 deg. |
| | b = 27.4756(7) Å beta = 90 deg. |
| | c = 27.4756(7) Å gamma = 90 deg. |
| Volume | 20741.6(9) Å$^3$ |
| Z, Calculated density | 4, 0.949 Mg/m$^3$ |
| Absorption coefficient | 10.332 mm$^{-1}$ |
| F(000) | 5624 |
| Crystal size | 0.15 × 0.15 × 0.15 mm |
| Theta range for data collection | 4.55 to 67.93 deg. |
| Limiting indices | −23 <= h <= 31, −32 <= k <= 29, −28 <= l <= 31 |
| Reflections collected/unique | 5524/5524 [R(int) = 0.000] |
| Completeness to theta = 66.60 | 98.7% |
| Absorption correction | Semi-empirical from equivalents |
| Max. and min. transmission | 0.3063 and 0.3063 |
| Refinement method | Full-matrix least-squares on F$^2$ |
| Data/restraints/parameters | 5524/4/38 |
| Goodness-of-fit on F$^2$ | 1.051 |
| Final R indices [I > 2sigma(I)] | $R_1 = 0.0732$, $wR_2 = 0.2048$ |
| R indices (all data) | $R_1 = 0.0768$, $wR_2 = 0.2085$ |
| Largest diff. peak and hole | 1.137 and −1.339 e. Å$^{-3}$ |

A number of embodiments of the invention have been described. Nevertheless, it will be understood that various modifications may be made without departing from the spirit and scope of the invention. Other embodiments are within the scope of the following claims.

What is claimed is:

1. A metal organic framework composition comprising: a metal ion component; and a bidentate ligand component having two anionic binding groups, wherein the two anionic binding groups are oriented 180 degrees from each other; wherein the metal ion component and the bidentate ligand component associate to form a face-centered cubic network; and wherein the metal ion component includes a rare earth metal ion.

2. The metal organic framework composition of claim 1, wherein the rare earth metal ion is La, Ce, Pr, Nd, Sm, Eu, Gd, Dy, Ho, Er, TM, Yb, Lu, Tb or Y.

3. The metal organic framework composition of claim 1, wherein the two anionic binding groups are the same.

4. A metal organic framework composition comprising: a metal ion component; and a bidentate ligand component having two anionic binding groups, wherein the two anionic binding groups are oriented 180 degrees from each other; wherein the metal ion component and the bidentate ligand component associate to form a face-centered cubic network; wherein the two anionic binding groups are different.

5. The metal organic framework composition of claim 1, wherein each of the anionic binding groups, independently, is carboxylate or tetrazolate.

6. The metal organic framework composition of claim 1, wherein the two anionic binding groups are linked by an aromatic group.

7. A metal organic framework composition comprising: a metal ion component; and a bidentate ligand component having two anionic binding groups, wherein the two anionic binding groups are oriented 180 degrees from each other; wherein the metal ion component and the bidentate ligand component associate to form a face-centered cubic network; and wherein the two anionic binding groups are linked by an hydrophobic group.

8. The metal organic framework composition of claim 7, wherein hydrophobic group is a fluoro group.

9. The metal organic framework composition of claim 1, wherein the metal ion component and the bidentate ligand form a 12-connected molecular building block.

10. A method of making a metal organic framework composition comprising: contacting a metal ion component with a bidentate ligand component having two anionic binding groups, wherein the two anionic binding groups are oriented 180 degrees from each other; wherein the metal ion component and the bidentate ligand component associate to form a face-centered cubic network; wherein the metal ion component includes a rare earth metal ion.

11. A method of making a metal organic framework composition comprising: contacting a metal ion component with a bidentate ligand component having two anionic binding groups, wherein the two anionic binding groups are oriented 180 degrees from each other; wherein the metal ion component and the bidentate ligand component associate to form a face-centered cubic network; wherein the bidentate ligand includes a hydrophobic group.

12. The method of claim 11, wherein hydrophobic group is a fluoro group.

13. The method of claim 10, wherein the rare earth metal ion is La, Co, Pr, Nd, Sm, Eu, Gd, Dy, Ho, Er, Tin, Yb, Lu, Tb or Y.

14. The method of claim 10, wherein the two anionic binding groups are the same.

15. A method of making a metal organic framework composition comprising: contacting a metal ion component with a bidentate ligand component having two anionic binding groups, wherein the two anionic binding groups are oriented 180 degrees from each other; wherein the metal ion component and the bidentate ligand component associate to form a face-centered cubic network; wherein the two anionic binding groups are different.

16. The method claim 10, wherein each of the anionic binding groups, independently, is carboxylate or tetrazolate.

17. The method of claim 10, wherein the two anionic binding groups are linked by an aromatic group.

18. The method of claim 10, wherein the metal ion component and the bidentate ligand form a 12-connected molecular building block.

19. The metal organic framework composition of claim 4, wherein the two anionic binding groups are linked by an aromatic group.

20. The method of claim 15, wherein the metal ion component and the bidentate ligand form a 12-connected molecular building block.

* * * * *